(12) United States Patent
Hanf et al.

(10) Patent No.: US 11,519,034 B2
(45) Date of Patent: Dec. 6, 2022

(54) NON-INVASIVE DIAGNOSTIC OF NON-ALCOHOLIC FATTY LIVER DISEASES, NON-ALCOHOLIC STEATOHEPATITIS AND/OR LIVER FIBROSIS

(71) Applicant: Genfit, Loos (FR)

(72) Inventors: Remy Hanf, Lille (FR); Genevieve Cordonnier, Templemars (FR); John Brozek, Saint-Amand-les-Eaux (FR)

(73) Assignee: Genfit, Loos (FR)

( * ) Notice: Subject to any disclaimer, the term of this patent is extended or adjusted under 35 U.S.C. 154(b) by 0 days.

(21) Appl. No.: 16/648,137

(22) PCT Filed: Sep. 14, 2018

(86) PCT No.: PCT/EP2018/074975
§ 371 (c)(1),
(2) Date: Mar. 17, 2020

(87) PCT Pub. No.: WO2019/053233
PCT Pub. Date: Mar. 21, 2019

(65) Prior Publication Data
US 2020/0216901 A1    Jul. 9, 2020

(30) Foreign Application Priority Data
Sep. 18, 2017 (EP) .................................. 17306201

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2011/0015080 A1* | 1/2011 | Golub | C12Q 1/6834 506/2 |
| 2015/0051145 A1* | 2/2015 | Darteil | A61K 31/381 514/6.5 |
| 2015/0133330 A1* | 5/2015 | Olaru | C12N 15/111 506/9 |

FOREIGN PATENT DOCUMENTS

WO    2016196945    8/2016

OTHER PUBLICATIONS

Liver International. 2015. 36:334-343 and Supporting Information Tables S1 and S5, published online Sep. 9, 2015 (Year: 2015).*
Heggard et al International Journal of Cancer. May 4, 2011. 102. 130: 1378-1386 (Year: 2011).*
Palmer et al. BMC Genomics. 2006. 7:115 (Year: 2006).*
Min et al BMC Genomics. 2010. 11:96 (Year: 2010).*
Murphy et al. Pathology, 2005, vol. 37(4), pp. 271-277) (Year: 2005).*
Tumilson et al. Molecular Neurobiology. 2014. 50: 545-558 (Year: 2014).*
Zhou et al Scientific Reports. Jun. 10, 2015. 6:11251 (Year: 2015).*
Fukui et al World J of Hepatology. 2015. 7(27): 2749-2756 (Year: 2015).*
U.S. Appl. No. 15/759,484, filed Mar. 12, 2018.
U.S. Appl. No. 16/089,835, filed Sep. 28, 2018.
U.S. Appl. No. 16/641,544, filed Feb. 24, 2020.
PCT/EP2018/074975, Dec. 12, 2018, International Search Report and Written Opinion.
Krattinger Regina et al. "Chenodeoxycholic acid significantly impacts the expression of miRNAs and genes involved in lipid, bile acid and drug metabolism in human hepatocytes", Life Sciences, Pergamon Press, Oxford, GB, vol. 56, May 10, 2016 (May 10, 2016), pp. 47-56.
Youwen Tan et al: "A Pilot Study of Serum MicroRNAs Panel as Potential Biomarkers for Diagnosis of Nonalcoholic Fatty Liver Disease", PLOS One, vol. 9, No. 8, Aug. 20, 2014 (Aug. 20, 2014), p. e105192.
Seungril Ro et al: "Tissue-dependent paired expression of miRNAs", Nucleic Acids Research, vol. 35, No. 17, Jul. 28, 2007 (Jul. 28, 2007), pp. 5944-5953.
Abdul M. Oseini et al.: "Therapies in non-alcoholic steatohepatitis (NASH)", Liver International, vol. 37, Jan. 1, 2017 (Jan. 1, 2017), pp. 97-103.
M. Noureddin et al.: "Review article: emerging anti-fibrotic therapies in the treatment of non-alcoholic steatohepatitis", Alimentary Pharmacology & Therapeutics., vol. 43, No. 11, Apr. 8, 2016 (Apr. 8, 2016), pp. 1109-1123.
Tingming Liang et al.: "Deep Sequencing of Small RNA Repertoires in Mice Reveals Metabolic Disorders-Associated Hepatic miRNAs", PLOS One, vol. 8, No. 11, Nov. 15, 2013 (Nov. 15, 2013), p. e80774.
Kendall R. Van Keuren-Jensen et al. "microRNA changes in liver tissue associated with fibrosis progression in patients with hepatitis C", Liver International, vol. 36, No. 3, Mar. 1, 2016 (Mar. 1, 2016), pp. 334-343.

* cited by examiner

*Primary Examiner* — Carla J Myers
(74) *Attorney, Agent, or Firm* — McDermott Will & Emery LLP

(57) ABSTRACT

The present invention relates to a novel non-invasive method for the diagnosis of a non-alcoholic fatty liver disease, in particular non-alcoholic steatohepatitis, and/or liver fibrosis.

12 Claims, 5 Drawing Sheets
Specification includes a Sequence Listing.

NON-INVASIVE DIAGNOSTIC OF NON-ALCOHOLIC FATTY LIVER DISEASES, NON-ALCOHOLIC STEATOHEPATITIS AND/OR LIVER FIBROSIS

RELATED APPLICATIONS

This application is a national stage filing under 35 U.S.C. § 371 of international application number PCT/EP2018/074975, filed on Sep. 14, 2018, which claims the benefit of priority to European Patent Application No. 17306201.9, filed on Sep. 18, 2017. The entire contents of each of the prior applications are herein incorporated by reference.

FIELD OF THE INVENTION

The present invention relates to a novel non-invasive method for the diagnosis of a non-alcoholic fatty liver disease, in particular non-alcoholic steatohepatitis, and/or liver fibrosis.

BACKGROUND OF THE INVENTION

Non-alcoholic fatty liver disease (NAFLD) is a silent disease defined as an accumulation of fat into the liver (steatosis) for causes other than excessive alcohol consumption. NAFLD is the most common cause of elevated aminotransferases in patients referred to hepatologists. NAFLD ranges from benign simple steatosis to a morbid condition for some patients, non-alcoholic steatohepatitis (NASH), where a necro/inflammatory process drives progressive accumulation of fibrosis into the liver, ultimately leading to cirrhosis, liver failure, hepatocellular carcinoma (HCC), liver transplant and liver death. Both on epidemiological and pathophysiological standpoints, NAFLD and NASH are closely associated with obesity, metabolic syndrome and type 2 diabetes. Therefore, in parallel with epidemics of obesity and type 2 diabetes, the prevalence of NAFLD and NASH has dramatically increased in the last decades and NASH is becoming the first cause of liver transplant in the US. Consequently, NASH is considered as a growing worldwide public health issue knowing that there is no optimal solution for diagnosis and no yet approved treatment for NASH.

While NAFLD may be diagnosed by detecting the presence of fat accumulation into the liver using ultrasound techniques, NASH and NASH-associated liver fibrosis can only be diagnosed by histological examination of a liver biopsy. At microscopic examination of a liver biopsy, NASH is defined by fatty acid accumulation (lipid droplets) associated with damaged hepatocytes (ballooning or necrosis of the hepatocytes) and signs of lobular inflammation. Although fibrosis is not a required histological feature for diagnosis of NASH, presence and staging of liver fibrosis is critical for assessing the severity of the disease and the risk of evolution to cirrhosis, HCC (hepatocellular carcinoma) and liver death which is the liver-related patient death.

Histological scoring/staging systems have been developed for assessing NAFLD activity level and fibrosis stage and estimating the risk of evolution to clinical liver outcomes. The NALFD-Activity-Score (NAS) has been developed for assessing the activity of the disease. The NAS is the sum of the unweighted biopsy's individual scores for steatosis (0 to 3), lobular inflammation (0 to 3), hepatocellular ballooning (0 to 2). According to Kleiner et al., (*Hepatology*, 2005; 41:1313-21), NAS is the sum of three histological scores made from liver biopsy slices:

S: Steatosis score: 0: <5%; 1: 5-33%; 2: 34-66% and 3: >66%

LI: Lobular Inflammation score (foci per 20× field): 0: none; 1: <2; 2: 2-4 and 3>4

HB: Ballooning degeneration score: 0: none; 1: few; 2: many cells/prominent ballooning.

Using this scoring system a patient with NASH has NAS≥3 and at least 1 point in steatosis, at least 1 point in lobular inflammation and at least 1 point in hepatocyte ballooning. A patient is considered as having an Active-NASH when NAS≥4 with at least 1 point in steatosis, at least 1 point in inflammation and at least 1 point in hepatocyte ballooning.

Localization and extent of fibrosis at histological exam signs the severity (advancement) of the disease and the NASH-CRN has developed a dedicated fibrosis staging system (Kleiner et al., Hepatology, 2005; 41:1313-21).

| | |
|---|---|
| Perisinusoidal or periportal fibrosis | 1 |
| Mild perisinusoidal fibrosis (zone 3) | 1a |
| Moderate perisinusoidal fibrosis (zone 3) | 1b |
| Portal/periportal fibrosis | 1c |
| Perisinusoidal and portal/periportal fibrosis | 2 |
| Bridging fibrosis | 3 |
| Cirrhosis | 4 |

Using this fibrosis staging system, patients with no or minimal fibrosis (F=0-1) are generally not considered at risk of cirrhosis, HCC or liver death. Patients with significant (F=2) and moderate fibrosis (F=3) are at increasing risk of developing cirrhosis, liver failure, HCC and liver death. Patient with compensated cirrhosis have severe fibrosis (F=4) and are at high risk of liver failure (decompensated cirrhosis), HCC and liver related-deaths.

Derived from these widely accepted two scoring and staging systems, special attention has been recently paid on the Activity Index (AI) which can be defined as the sum of the lobular inflammation score and the hepatocyte ballooning scores. In addition Munteanu et al., *Aliment Pharmacol Ther.*, 2016, 44(8):877-89 have proposed SAF signature to report separately scores of Steatosis, disease Activity and Fibrosis.

The diagnostic of NAFLD and NASH, and scoring of disease activity using the aforementioned NAS, AI and staging of liver fibrosis requires liver biopsies, which have a number of obvious drawbacks precluding their routine use. Indeed, liver biopsy is an invasive procedure that may be cumbersome, worrisome and painful for the patient and liver biopsy is associated with risks of hemorrhages and even deaths. Accordingly, because of growing NASH and liver fibrosis epidemic and because biopsy cannot be seen as a sufficiently efficient and safe procedure, there is an urgent need for new non-invasive methods for diagnosis of NAFLD, NASH and/or liver fibrosis.

Ultrasound and imaging techniques (ultrasonography, controlled attenuation parameter, Magnetic Resonance Imaging (MRI), and the MRI-estimated proton density fat fraction (MRI-15 DPFF)) have been developed to diagnose NAFLD. However, these techniques are limited by both interobserver and intraobserver variability, by cost and/or are time consuming. In addition, MRI-DPFF is not routinely available and is too complicated to be used in clinical practice. Moreover, fibrosis stage is associated with all-cause mortality in a dose dependent manner, with increased risk apparent in patients with F2 fibrosis. Ultrasound-based 20 elastography such as Fibroscan and shear wave elastography has moderate to high accuracy in diagnosing advanced fibrosis or cirrhosis. However F2 fibrosis is not an advanced fibrosis stage and thus cannot be accurately detected with these techniques.

Besides ultrasound and imaging techniques, intense efforts have been paid for identification and validation of new circulating biomarkers for a reliable, simple and cost-effective non-invasive detection of NAFLD, NASH and/or liver fibrosis. The following table lists individual biomarkers which have been reported as modulated in NAFLD/NASH and/or liver fibrosis.

| Hepatocyte function | Adipose tissue | Metabolism | Oxidative stress/apoptosis | Fibrosis | Inflammation |
|---|---|---|---|---|---|
| ALT | Adiponectin | Fasting plasma glucose | Malondialdehyde | Fibronectin | TNFa |
| AST | Leptin | | TBARS | Hyaluronic acid | IL1b, IL6, |
| ALP | Resistin | Fasting insulin | Ox LDL | Type IV collagen | IL8, IFNg, |
| GGT | | HOMA index | CK18-M30 | | TGFb |
| Haptoglobin | | Trglycerides | CK18-M65 | PIIINP | hs-CRP |
| Albumin | | HDL-Choleterol | Ferritin | TIMP-1 | MCP1 |
| Bilirubin | | VLCL-C | YKL-40 (CHI3L1) | | sCD14 |
| Platelet Count | | Apolipoproteins (ApoA1, ApoB, ApoCIII) | | | |

Several studies have suggested that some of these serum biomarkers had better diagnostic values than the routine serum markers of liver dysfunction like transaminases (Naveau S. et al., Clin Gastroenterol Hepatol., 2005; 3(2): 167-74; Castera L. et al., J. Hepatol. 2000; 32:412-8; Annoni G. et al. Hepatology. 1989; 9:693-7; Nojgaard C. et al. J Hepatol. 2003;39: 179-86; Chossegros P. 1995; 22(2 Suppl): 96-9). However none of these studies has really identified and validated a powerful biomarker for diagnosing NAFLD, NASH and/or liver fibrosis. Trying to improve diagnostic performances, multiparametric scores have been generated combining several biomarkers and/or routine variables but their diagnostic performances for identification of patient with NAFLD, NASH and/or liver fibrosis remains largely improvable.

NASH is associated with faster fibrosis progression than NAFLD and is currently the main target for pharmacological treatment. NASH patients are more likely to develop cirrhosis and die from cardiovascular and liver-related causes, with the prognostic deteriorating as the 15 fibrosis stage progresses (Ekstedt et al, 2015). Despite the large number of serum biomarkers, combination panels, and imaging biomarkers that have been proposed, the identification of effective, less invasive, and more affordable methods for diagnosing and monitoring NAFLD, NASH and liver fibrosis are still needed, in particular methods confirmed with an independent clinical validation panel.

Identifying patients who are at risk of developing HCC, cirrhotic complications and liver-related deaths, is the ultimate reason for liver assessment.

SUMMARY OF THE INVENTION

The inventors have conducted several very fine and complete analysis of different cohorts of patients to provide novel and highly sensitive non-invasive diagnostic and monitoring methods of non-alcoholic fatty liver disease (NAFLD), non-alcoholic steatohepatitis (NASH) and liver fibrosis. The data provided herein demonstrate that miR-452 is a potent circulating biomarker linked to NAFLD, NASH and/or liver fibrosis. This biomarker was validated in three independent clinical cohorts. Therefore, the methods of the present invention allow diagnosing, monitoring and risk classifying a subject as suffering from NAFLD, NASH and/or liver fibrosis. The inventors also provide a method for the diagnosis, monitoring and risk classification of subjects potentially suffering from NAFLD, NAFL, NASH and/or liver fibrosis. The methods of the present invention may also allow the development of new therapeutic treatments.

Accordingly, the invention provides a method for the diagnosis of a NAFLD, NASH or liver fibrosis in a subject, comprising determining the level of miR-452 in a body fluid sample of a said subject.

These methods are based on the determination of the level of miR-452 in a body fluid of the subject. In all the methods and embodiments presented herein, the miR-452 microRNA implemented in the present invention may be a hsa-miR-452 microRNA, such as a hsa-miR-452 selected from the group consisting of hsa-miR-452-5p and hsa-miR-452-3p. In a particular embodiment, the level of hsa-miR-452-5p is determined. In all the methods and embodiments presented herein, the body fluid sample may be a sample of blood, of a blood-derived fluid (such as serum and plasma, in particular platelet-free plasma, e.g. a cell-free, citrate-derived platelet-free plasma sample), of saliva, of cerebrospinal fluid or of urine. In a particular embodiment, the body fluid is plasma or serum, deprived of platelets or not.

In the methods of the present invention, the body fluid level of miR-452 in the subject may be compared to a reference level of miR-452. The "reference level" denotes a predetermined standard or a level determined experimentally in a sample processed similarly from a reference subject. Depending of the purpose of the methods of the present invention, the reference subject may be a healthy subject, a subject having NAFLD but no NASH, a subject having NASH but no active NASH, or a subject with no or minimal liver fibrosis. The reference subject may also be a placebo treated patient. The reference level may also be the level of miR-452 determined in a similarly processed body fluid sample obtained in the past from the same subject, allowing determining the evolution of NAFLD, NAFL, NASH or liver fibrosis in the subject, in particular allowing determining the evolution of the disease activity or fibrosis, or the efficiency of the treatment of the disease, depending on the method being implemented.

In a particular embodiment, the diagnosis and/or detection of NAFLD, or the diagnosis and/or detection of a potential NAFLD, in a subject is based on the detection of an increased level of miR-452 in the body fluid sample relative to a reference level measured in healthy subjects with no hepatic steatosis.

In a particular embodiment, the diagnosis and/or detection of NAFL, or the diagnosis and/or detection of a potential NAFL, in a subject is based on the detection of an increased level of miR-452 in the body fluid sample relative to a reference level measured in healthy subjects with no hepatic steatosis, no lobular inflammation and no hepatocyte ballooning.

In another particular embodiment, the diagnosis and/or detection of NASH, or the diagnosis and/or detection of a potential NASH, in a subject is based on the detection of an increased level of miR-452 in the body fluid sample relative to a reference level measured in a non-NASH subject such as a healthy subject, a subject with a NAS<3 or a subject with at least one component of NAS scored at 0.

In another embodiment, the diagnosis and/or detection of Active-NASH, or the diagnosis and/or detection of a potential Active-NASH, in a subject is based on the detection of an increased level of miR-452 in the body fluid sample relative to a reference level measured in a healthy subject, a subject with NAS<4 or a subject with at least one component of NAS scored at 0. In a particular embodiment, for the diagnosis and detection of Active-NASH or of potential Active-NASH, the reference level is the level of miR-452 measured in a subject with NAS=3, 1 point of steatosis, 1 point in lobular inflammation and 1 point in the hepatocyte ballooning scores.

In a further embodiment, the diagnosis and detection of liver fibrosis (F≥1), or of potential liver fibrosis (F≥1), in a subject is based on the detection of an increased level of miR-452 in the body fluid sample relative to a reference level measured in a healthy subject with no liver fibrosis (F=0).

In another embodiment, the diagnosis and detection of significant (F=2), moderate (F=3) or severe (F=4; i.e. cirrhosis) liver fibrosis, or of potential significant liver fibrosis, potential moderate liver fibrosis, or potential severe liver fibrosis, in a subject is based on the detection of an increased level of miR-452 in the body fluid sample relative to a reference level measured in a subject with no (F=0) or minimal (F=1) liver fibrosis.

In another embodiment, the diagnosis and detection of significant (F=2), moderate (F=3), or severe (F=4) liver fibrosis, or of potential significant liver fibrosis, potential moderate liver fibrosis, or potential severe liver fibrosis, in a subject is based on the detection of an increased level of miR-452 in the body fluid sample relative to a reference level measured in a subject with minimal fibrosis (F=1). In another particular embodiment, the reference level is measured in a subject with F=1a, 1b or 1c.

In another embodiment, the diagnosis and detection of significant liver fibrosis, or of potential significant liver fibrosis, in a subject is based on the detection of an increased level of miR-452 in the body fluid sample relative to a reference level measured in a subject with minimal liver fibrosis.

In another embodiment, the diagnosis and detection of moderate liver fibrosis or of potential moderate liver fibrosis, in a subject is based on the detection of an increased level of miR-452 in the body fluid sample relative to a reference level measured in a subject with significant liver fibrosis.

In another embodiment, the diagnosis and detection of severe liver fibrosis, or of potential severe liver fibrosis, in a subject is based on the detection of an increased level of miR-452 in the body fluid sample relative to a reference level measured in a subject with moderate liver fibrosis.

According to a further object, the invention relates to a method for the classification of a subject as being potential receiver (to be treated, or TBT) or non-receiver (not to be treated, or NTBT) of a treatment for NAFLD, NASH or liver fibrosis, based on the detection of an increased level of miR-452 in the body fluid sample relative to a reference level of miR-452 measured in NTBT patients as defined below.

In a further embodiment, the invention also provides a method for the determination of NAFLD activity level, NASH activity level and/or liver fibrosis stage in a subject, based on the determination of the level of miR-452 in a body fluid sample of a subject.

Through another aspect, the invention also allows the clinical prognostic of fibrosis, which is the prognostic of the risk of liver fibrosis evolution to cirrhosis and other liver outcomes (such as HCC and liver-related deaths) of a NAFLD or NASH patient based on the level of miR-452 determined in a body fluid sample of a subject.

The invention also provides a method for monitoring the evolution of NAFLD activity level, NASH activity level, and/or liver fibrosis stage in a subject, based on the evolution of the level of miR-452 in a body fluid sample of the subject relative to a reference level of miR-452 from one or more body fluid sample(s) collected in the same subject in the past. In this method, an increase of the level of miR-452 indicates that the disease activity and fibrosis grow up whereas a decrease of the level of miR-452 indicates that the disease activity and fibrosis decline.

The invention further provides a method for determining the efficiency of a treatment of NAFLD, NASH or liver fibrosis in a subject based on the evolution of the level of miR-452 in a body fluid sample of the subject relative to a reference level of miR-452 from one or more body fluid sample(s) collected in the same subject in the past. In this method, an increase of the level of miR-452 or a stable level of miR-452 indicates that the treatment is not efficient whereas a decrease of the level of miR-452 indicates that the treatment is efficient. In another embodiment of this method, a stable level of miR-193 may also indicate that the treatment is efficient in stabilizing the NASH, NAFLD or liver fibrosis state of the subject, thereby decreasing the risk for the subject to evolve towards critical outcomes such as cirrhosis, HCC or liver-related deaths.

The invention further provides a method for predicting the response of a subject (e.g. prediction of changes in NAFLD, NASH activity and liver fibrosis stage) to a specific treatment (responder subject) based on the detection of a differential level of miR-452 in the body fluid sample relative to a reference level measured in a non-responder subject.

TBT1=Steatosis, lobular inflammation and hepatocyte ballooning score ≥1, NAS≥4, F≥1

TBT2=Steatosis, lobular inflammation and hepatocyte ballooning score ≥1, NAS≥4, F≥2

TBT7=Steatosis, lobular inflammation and hepatocyte ballooning score ≥1, NAS≥4, F=1b, 1c, 2, 3 or 4

Figure 2:
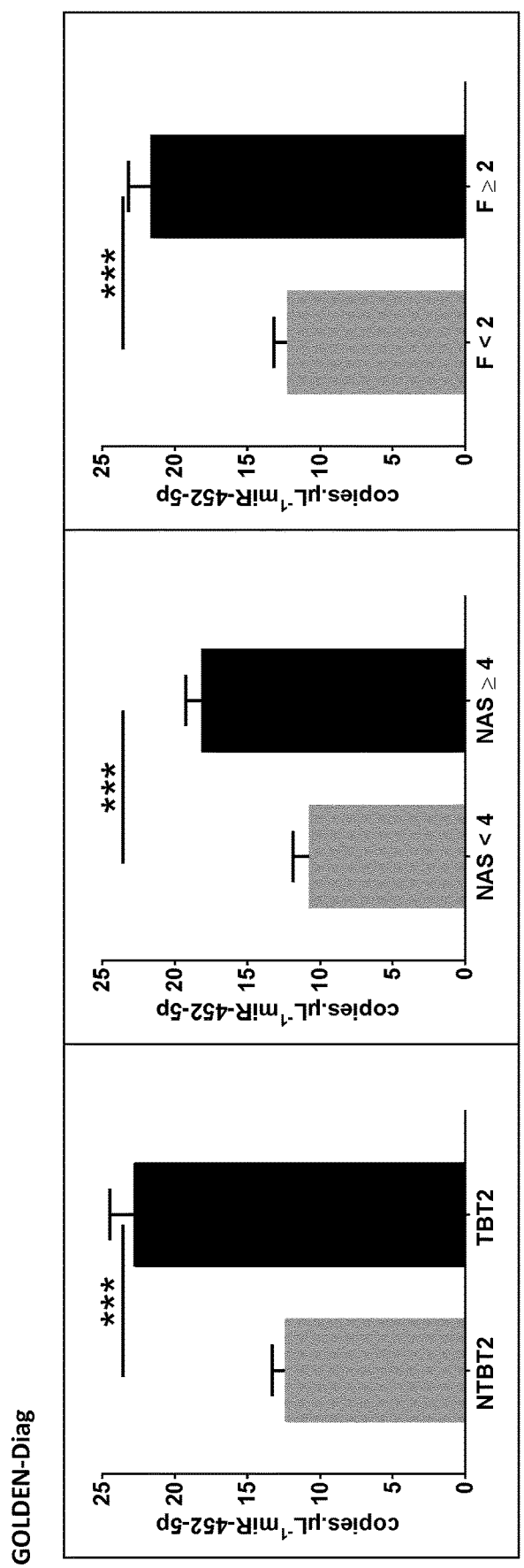

FIG. 2: Serum level of hsa-miR-452-5p in NTBT2 and TBT2 patients (left), in patients with NAS<4 (n=56) and NAS≥4 (n=214) (middle) and in patients with F<2 (n=145) and F≥2 (n=125) (right) of GOLDEN-DIAG. Results are expressed as Mean±SEM. Statistical significance was calculated using Mann Whitney test: ***, p value<0.001.

Figure 3:
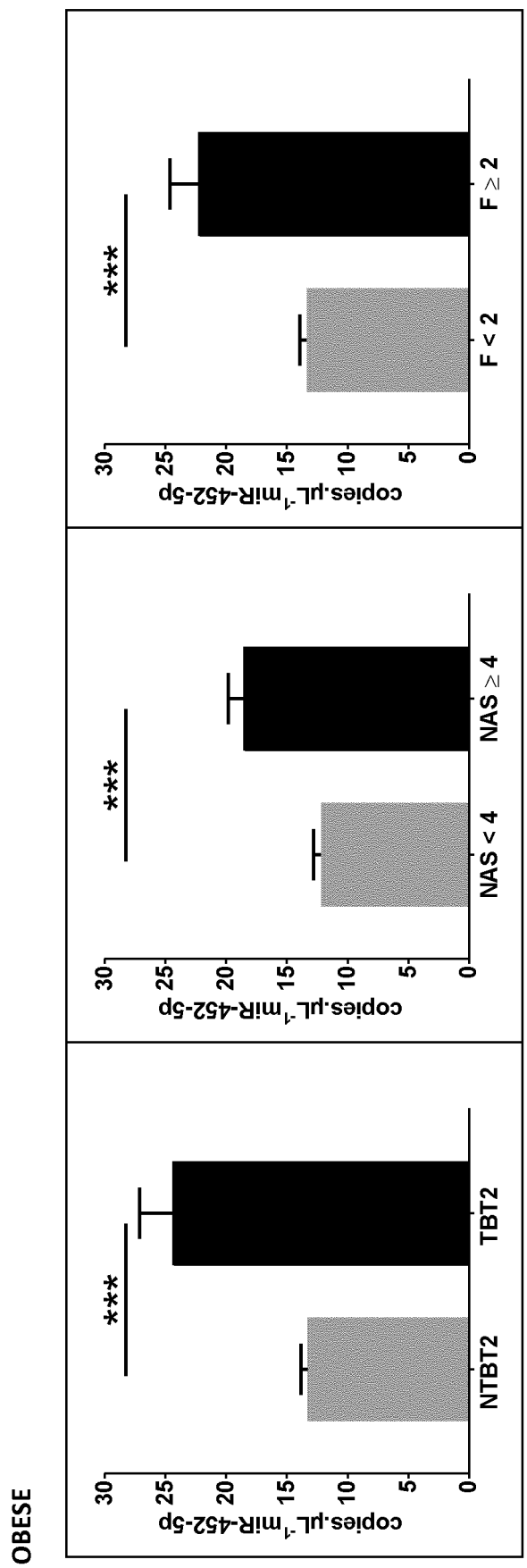

FIG. 3: Serum level of hsa-miR-452-5p in NTBT2 and TBT2 patients (left), in patients with NAS<4 (n=121) and NAS≥4 (n=129) (middle) and in patients with F<2 (n=190) and F≥2 (n=59) (right) of OBESE. Results are expressed as Mean±SEM. Statistical significance was calculated using Mann Whitney test: ***, p value<0.001.

Figure 4:
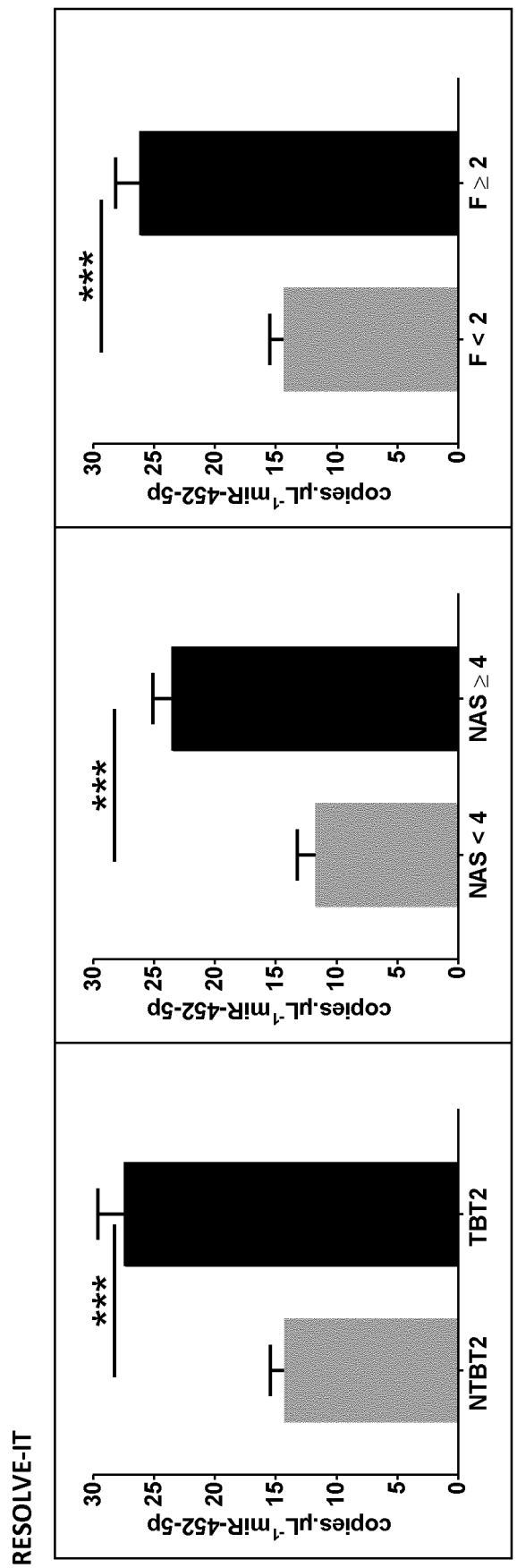

FIG. 4: Serum level of hsa-miR-452-5p in NTBT2 and TBT2 patients (left), in patients with NAS<4 (n=50) and NAS≥4 (n=212) (middle) and in patients with F<2 (n=108) and F≥2 (n=154) (right) of RESOLVE-IT. Results are expressed as Mean±SEM. Statistical significance was calculated using Mann Whitney test: ***, p value<0.001.

Figure 5:
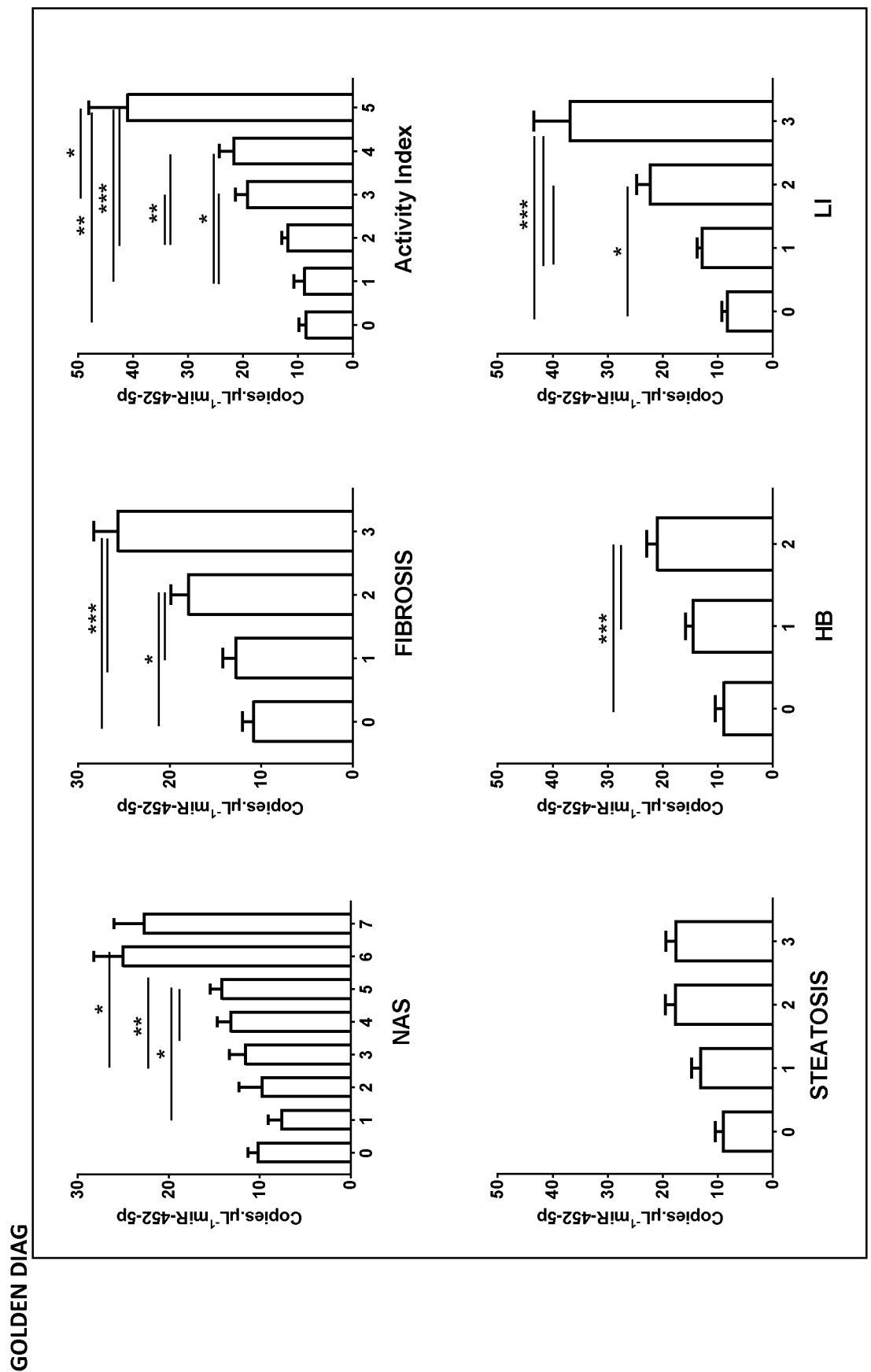

FIG. 5: Correlation between serum levels of hsa-miR-452-5p with NAS, Fibrosis stage, Activity Index, Steatosis score, Hepatocyte Ballooning score, Lobular Inflammation score in patients of GOLDEN-DIAG cohort at inclusion. Results are expressed as Mean±SEM. Statistical significance was calculated using Kruskal Wallis ANOVA test followed by Dunn's multiple comparison test: *, p value<0.05;  p value<0.005; *, p value<0.001

DETAILED DESCRIPTION OF THE INVENTION

The inventors provide a new method for the diagnosis, monitoring and risk classification of subjects suffering or potentially suffering from NAFLD, NASH and/or liver fibrosis.

The present invention stems from the very fine analysis of patients' biopsies during a clinical trial, to correlate the presence or level of circulating biological markers and to classify patients as to be treated or not to be treated. In particular the present invention non-limitatively defines three classes of NASH patients to be treated. These patients are classified with respect to the scoring of NASH characteristics.

The experimental data provided herein surprisingly identify miR-452 as a circulating biomarker for NAFLD, NAFL, NASH and/or liver fibrosis from two large independent cohorts of patients, namely GOLDEN-DIAG (N=270 at inclusion; N=223 at week-52) and OBESE cohort (N=253) with scored liver biopsies and corresponding blood, plasma and serum samples. The results were validated in a third independent cohort RESOLVE-IT (N=263).

The invention will now be presented in greater details.

Definitions

According to the present invention, the terms "NAFLD" or "Non Alcoholic Fatty Liver Disease" refers to a condition in which fat is deposited in the liver (hepatic steatosis), with or without signs of inflammation and fibrosis, in the absence of excessive alcohol consumption.

According to the invention, the terms "NAFLD activity level" refer to NAFLD progression and is defined by an increase in the steatosis score, as defined herein. NAFLD activity level also refers to of NAFLD progression towards NASH or Fibrosis and NASH severity According to the present invention, the terms "NAFL" or "Non Alcoholic Fatty Liver" refers to a condition in which fat is deposited in the liver (hepatic steatosis), without signs of inflammation and fibrosis, in the absence of excessive alcohol consumption.

According to the invention, the term "steatosis" refers to the process describing the abnormal retention of lipids or fat accumulation within the liver.

According to the invention, the term "NASH" or "Non-Alcoholic SteatoHepatitis" refers to a NAFLD condition characterized by the concomitant presence of liver steatosis, hepatocyte ballooning and liver inflammation at histological examination, (i.e. NAS≥3, with at least 1 point in steatosis, at least 1 point in lobular inflammation and at least 1 point in the hepatocyte ballooning scores) in the absence of excessive alcohol consumption and after excluding other liver diseases like viral hepatitis (HCV, HBV) . . . .

According to the invention, the terms "NASH activity level" refer to NASH progression and is defined by an increase in the NAS score above the minimal parameters for defining a NASH, which are S=1, LI=1 and HB=1. NASH activity level also refers to NASH progression towards irreversible NASH and/or fibrosis and NASH severity.

According to the invention, the term "Active-NASH" refers to a NASH characterized by a NAS≥4, with at least 1 point in steatosis score, at least 1 point in the lobular inflammation score and at least 1 point in the hepatocyte ballooning scores.

According to the present invention, the term "hepatocellular ballooning" is usually defined, at the light microscopic level, based on hemotoxylin and eosin (H&E) staining, as cellular enlargement 1.5-2 times the normal hepatocyte diameter, with rarefied cytoplasm. It refers more generally to the process of hepatocyte cell death.

According to the present invention, the term "lobular inflammation" refers to the presence of lobular inflammatory foci (grouped inflammatory cells) at microscopic examination of a hematoxylin and eosin (H&E) stained slice of a liver biopsy.

According to the present invention, the "NAFLD-Activity score" or "NAS" refers to the sum of steatosis, hepatocellular ballooning, lobular inflammation scores, as follows:

S: Steatosis score: 0: <5%; 1: 5-33%; 2: 34-66% and 3: >66%;
LI: Lobular Inflammation score (foci/×20 field): 0: none; 1: <2; 2: 2-4 and 3: >4;
HB: Ballooning degeneration score: 0: none; 1: few; 2: many cells/prominent ballooning.

According to the present invention, the "Activity index" refers to the sum of hepatocellular ballooning and lobular inflammation scores.

According to the present invention, the term "fibrosis" or "liver fibrosis" refers to the presence of fibrous connective tissue at microscopic examination of a stained (H&E, trichrome or picrosirius red staining) slice of a liver biopsy.

In the context of the present invention, the term "fibrosis stage" denotes the localization and extent of fibrosis at histological exam, as follows:

| | |
|---|---|
| Perisinusoidal or periportal fibrosis | 1 |
| Mild perisinusoidal fibrosis (zone 3) | 1a |
| Moderate perisinusoidal fibrosis (zone 3) | 1b |
| Portal/periportal fibrosis | 1c |
| Perisinusoidal and portal/periportal fibrosis | 2 |
| Bridging fibrosis | 3 |
| Cirrhosis | 4 |

Alternatively, the fibrosis stage may be referred to as follows in the context of the present invention:
F=0: no fibrosis
F=1: minimal fibrosis
F=2: significant fibrosis F=3: moderate fibrosis F=4: severe fibrosis (i.e. cirrhosis)

According to the present invention, "To-Be-Treated subject" or "TBT subject" is a subject whose disease activity score (e.g. NAS or Activity Index) and/or liver fibrosis stage make the subject eligible to a treatment for NAFLD, NAFL, NASH and/or liver fibrosis (such as for NAFLD, NASH and/or liver fibrosis). By opposition a "Not-To-be-treated subject" or "NTBT subject" is a subject whose disease activity score (e.g. NAS or Activity Index) and/or liver fibrosis stage is not high enough to deserve treatment for NAFLD, NAFL, NASH and/or liver fibrosis (such as for NAFLD, NASH and/or liver fibrosis). Therefore, a TBT subject is also referred to as "receiver" or "potential receiver" for a NAFLD, NAFL, NASH and/or liver fibrosis treatment (such as for a NAFLD, NASH and/or liver fibrosis treatment). In the present invention, preferential TBT subjects are:

i) subjects with NASH, ii) subjects with Active-NASH, iii) subjects with significant, moderate or severe liver fibrosis, iv) subjects with NASH and fibrosis.

The definition encompasses various NASH activity scores and fibrosis stages defining different variants of the invention.

Preferential variants of the invention are detailed as follows.

First TBT Variant (TBT2):

A TBT2 subject is defined as a subject presenting the following liver biopsy-derived grades:

S≥1

HB≥1

LI≥1

NAS (NAFLD Activity Score)≥4 fibrosis stage≥2 (such as a fibrosis stage equal to 2, 3 or 4, in particular 2 or 3).

By extension a NTBT2 subject differs from a TBT2 subject in at least one point lesser grade in steatosis, hepatocyte ballooning, lobular inflammation scores, NAS and/or fibrosis stage. For the sake of clarity, a NTBT2 subject may be, for example, a NASH subject having NAS=4, S≥1, LI≥1, HB≥1 and a fibrosis stage of 1 (such as a fibrosis stage 1a, 1b or 1c), or a NAS of 3 and a fibrosis stage≥2 (such as a fibrosis stage equal to 2, 3 or 4), or any other combination of scores as defined above Second TBT Variant (TBT1):

A TBT1 subject is defined as a subject presenting the following liver biopsy-derived grades:

S≥1

HB≥1

LI≥1

NAS (NAFLD Activity Score)≥4 fibrosis stage≥1 (such as a fibrosis stage equal to 1, 2, 3 or 4).

By extension a NTBT1 subject differs from a TBT1 subject in at least one point lesser grade in steatosis, hepatocyte ballooning, lobular inflammation scores, NAS and/or fibrosis stage. For the sake of clarity, a NTBT1 subject may be, for example, a NASH subject having 35 NAS=4, S≥1, LI≥1, HB≥1 and a fibrosis stage of 0, or a NAS of 3 and a fibrosis stage≥1 (such as a fibrosis stage equal to 1a, 1b or 1c, 2, 3 or 4), or any other combination of scores as defined above.

Third TBT Variant (TBT7):

A TBT7 subject is defined as a subject presenting the following liver biopsy-derived grades:

S≥1

HB≥1

LI≥1

NAS (NAFLD Activity Score)≥4 fibrosis stage=1b, 1c, 2, 3 or 4.

By extension a NTBT7 subject differs from a TBT7 subject in at least one point lesser grade in steatosis, hepatocyte ballooning, lobular inflammation scores, NAS and/or fibrosis stage. For the sake of clarity, a NTBT7 subject may be, for example, a NASH subject having a NAS=4, S≥1, LI≥1, HB≥1 and a fibrosis stage of 0 or 1a, or a NAS of 3 and a fibrosis stage equal to 1b, 1c, 2, 3 or 4, or any other combination of scores as defined above.

In a particular embodiment, the miR-452 microRNA implemented in the present invention is selected from the group consisting of hsa-miR-452-5p, hsa-miR-452-3p, whose sequences are available from the miRBase database (mirbase.org) under the miRBase Accession numbers MIMAT0001635 (SEQ ID NO:1) and MIMAT0001636 (SEQ ID NO:2) respectively.

In another embodiment, the miR-452 microRNA implemented in the present invention is a miR-452 stem-loop form, also named HGNC:MIR452, whose sequence is available from the miRBase database (mirbase.org) under the miRBase Accession number MI0001733 (SEQ ID NO:3).

```
SEQ ID NO: 1:
AACUGUUUGCAGAGGAAACUGA

SEQ ID NO: 2:
CUCAUCUGCAAAGAAGUAAGUG

SEQ ID NO: 3:
GCUAAGCACUUACAACUGUUUGCAGAGGAAACUGAGACUUUGUAACUAUG

UCUCAGUCUCAUCUGCAAAGAAGUAAGUGCUUUGC
```

In a particular embodiment, the mir-452 microRNA implemented in the present invention is hsa-miR-452-5p.

Samples and Sample Preparation

According to the present invention, the term "body fluid sample" denotes any body fluid sample obtained from a subject such as blood and blood-derived fluids (such as plasma and serum), lymphatic fluid, cerebrospinal fluid, synovial fluid, urine, saliva, mucous, phlegm and sputum. In a particular embodiment, the body fluid is selected from blood and blood-derived fluids (such as plasma and serum), saliva, cerebrospinal fluid and urine. In a particular embodiment the body fluid sample is a blood or blood-derived fluid (such as plasma and serum), saliva, cerebrospinal fluid or urine. In a further particular embodiment, the body fluid is blood, plasma or serum. A body fluid sample may be collected by any suitable means. Suitable body fluids may be acellular fluids. Such acellular body fluids are generally produced by processing a cell-containing body fluid by, for example, centrifugation or 5 filtration, to remove the cells. Typically, an acellular body fluid contains no intact cells however, some may contain cell fragments or cellular debris. The body fluid sample may be used immediately or may be stored for later use. Any suitable storage method known in the art may be used to store the body fluid sample: for example, the sample may be frozen at about −20° C. to about −80° C.

miRNA Isolation and Quantification

Total RNA including miRNA can be purified from a sample by various methods of extraction which include either: phenol:chloroform extraction followed by alcohol precipitation (TRIzol), phenol:chloroform followed by solid-phase extraction (column-based; e.g. miRVana and miRNeasy) and solid-phase separation with/without affinity resin (Norgen total and Isolate II) magnetic particles, or direct lysis methods. In the practice of the present invention, miRNA were extracted with miRVana Paris extraction kit for subsequent RTqPCR analysis or captured with specific probes for further HTG Edge Sequence analysis Next, miRNAs are detected in clinical samples using any technique available to those skilled in the art, such as sequencing-based, amplification-based, or hybridization-based methods. Common approaches to miRNA clinical testing include small RNA sequencing (Hafner et al, 2012; Vigneault et al, 2012), HTG Edge Whole Transcriptome assay, a next-generation 25 sequencing-based miRNA profiling platform (Lizarraga et al, 2016; Satake et al, 2018), quantitative miRNA real-time reverse-transcription PCR (qRT-PCR) (Chen et al, 2005), miRNA microarray (Castoldi et al, 2007), multiplexed miRNA detection with color-coded probe pairs (NanoString n Counter expression system) (Geiss et al, 2008), droplet digital PCR (ddPCR) after reverse transcription (Miotto et al, 2014), and miRNA in situ hybridization 30 (Nelson et al, 2006). The level of the miR-193 may be determined by conventional methodologies well known in the art, such as immunoassays (e.g. ELISA), or molecular biology assays (quantitative RT-PCR or Next-Generation-Sequencing) or biochemical assays (colorimetric assays or others). In a particular embodiment of the method of the present invention, miRNA are detected by HTG Edge whole transcriptome assays or HTG Edge 35 sequencing, and RT-qPCR.

In the practice of the present invention, any of the above described methods may further comprise normalizing the level of miR-452 in the body fluid sample from the subject and in the reference to the level or a microRNA whose level does not vary in NAFLD, NASH and/or liver fibrosis subjects relative to healthy patients. To reduce potential source of technical variability, a spike-in or exogenous synthetic micro-RNA of known sequence and quantity, such as *C. elegans* miR-39, may be added to the sample before RNA extraction. The spike-in or exogenous synthetic micro-RNA may be a miRNA that is not expressed in human samples, such as Caenorhabditis elegans cel-miR-38 or Arabidopsis thaliana ath-miR-159a. These synthetic micro-RNA may be added after addition of the lysis buffer in blood derived samples before RNA extraction and provide a process control for technical normalization. The efficiency of RNA extraction, complementary DNA synthesis and PCR amplification can be therefore monitored using these exogenous synthetic micro-RNAs A micro-RNA normalizer or small non coding RNA controls for the normalization of qPCR data, representing endogenous controls that are affected by the same sources of variability as the target genes, during all the steps of the experimental pipeline, may be used to normalize the level of the target miRNA, miR-452.

A standard protocol for measuring miR-452 by quantitative RT-PCR is provided. Briefly, the measures are carried out from total RNA extracted from a body fluid sample such as blood, plasma or serum sample, in particular a cell-free, citrate-derived platelet-free plasma sample. An appropriate internal control (such as a micro-RNA of known sequence and quantity, e.g. *C. elegans* miR-39) may be added to the sample before RNA extraction. Cq values are determined using quantitative RT-PCR. Commercial kits are available for conducting such assays. For example, the Taqman miRNA RT-qPCR assay: Taqman MicroRNA Reverse transcription Kit, TaqMan MicroRNA Assay 20×, and TaqMan Universal Master Mix II (Applied Biosystems) may be used according to the manufacturer's instructions. Reverse transcription may be performed using readily available PCR systems, such as the GeneAmp® PCR System 9700 thermal cycler (Applied Biosystems), with appropriate cycling parameters such as 16° C. for 30 minutes followed by 42° C. for 30 minutes and 85° C. for 5 30 minutes before holding at 4° C. The reverse transcription may be implemented in the multiplexed format. Quantitative PCR is then conducted using a quantitative PCR system such as the CFX96TM Real-Time System (C1000 Touch™ Thermal Cycler, Bio-Rad). Preferentially, quantitative PCR is conducted using a CFX96-Real-Time PCR Detection System—C1000—In Vitro Diagnostic (IVD) certified, Bio-Rad. Cycling conditions may be the 35 following: 95° C. for 10 minutes followed by 95° C. for 15 sec and 60° C. for 60 sec for a total of 50 cycles and then 30° C. for 30 sec. Cq determination mode may be, for example, the Regression mode in the quantitative PCR system. In a particular embodiment, the Cq value determined according to the method of the invention is the Cq value which is obtainable using the above specific parameters and material. Cq values of samples may be excluded from the analysis if values are above the maximum Cq of the standard curve of each miRNA. The standard curve may be used to assess the PCR reaction efficiency. Serial dilutions may be performed over eight points starting from the most concentrated cDNA sample, to ensure the standard curve covers all potential template concentrations that may be encountered during the study. The standard curve may be constructed by plotting the log of the starting quantity of the template against the Cq values obtained. To obtain absolute quantitative data synthetic miRNAs (e.g. from Integrated DNA Technologies, 5'Phosphate, 3'OH, HPLC purified) diluted, for example, at 3.125 fmol/mL and 5 µL, may be used for reverse transcription concurrently with RNA extracted from serum samples. The product may then be serially diluted and PCR may be performed on all samples (standards and serum-derived RNA). Standard curve may be performed in simplicate, duplicate or triplicate and used to convert Cq data in copies/µL of fluid.

Alternatively, the delta Ct (Cycle threshold) or delta Cq (Cycle quantification) method may be used to estimate the level of miR-452. Delta Ct or delta Cq corresponds to the difference between the Ct or the Cq of the target in a patient tested sample and the Ct or the Cq of the target in a reference sample (i.e. healthy subjects, referent sample.)

Alternatively, the level of the miR-452 may be determined by RT-qPCR using stem-loop reverse transcription (RT) reaction combined with TaqMan qPCR, or with a poly(A)-tailed RT combined with SYBR Green detection and Lock Nucleic Acid (LNA) primers.

Methods of the Invention

In all the following aspects, embodiments and variants, a preferred embodiment relates to the determination of the level of hsa-miR-452 in a blood, serum or plasma sample. A preferable variant of this aspect relates to the determination of the level of hsa-miR-452-5p.

The present invention relates to a method for the diagnosis or detection of a NAFLD in a subject, comprising determining the level of miR-452, in a body fluid sample of said subject. The present invention also relates to a method for the diagnosis or detection of a potential NAFLD in a subject, comprising determining the level of miR-452, in a body fluid sample of said subject. In a particular embodiment, NAFLD or potential NAFLD is detected based on increased level of miR-452 in the body fluid sample from the subject, relative to a reference level measured in a sample from a subject with no hepatic steatosis. In a further particular embodiment, the diagnosis or detection of NAFLD or potential NAFLD is based on the detection of an increased level of miR-452 in a body fluid sample relative to levels generally measured in healthy subjects with no hepatic steatosis. In a particular embodiment, the method further comprise a step of confirming that the subject suffers from NAFLD. Such confirmation may be implemented according to any method known by those skilled in the art, such as by conducting a liver biopsy or by ultrasound or imaging techniques (such as ultrasonography, controlled attenuation parameter measurement by transient elastography (Fibroscan), Magnetic Resonance Imaging (MRI), MRI-estimated proton density fat fraction (MRI-DPFF), and the Magnetic resonance spectroscopy density fat fraction (MRS-DPFF)). Alternatively, several indices and scores may assess hepatic steatosis, including, without limitation:

the fatty liver index (FLI) which comprises BMI, waist circumference and serum levels of triglycerides and gamma glutaryl transferase (GGT), the hepatic steatosis index (HIS) which includes serum aspartate aminotransferase (AST): alanine aminotransferase (ALT) ratio, BMI, gender and presence of diabetes mellitus, the NAFLD liver fat score (metabolic syndrome, type 2 diabetes, fasting serum insulin and AST, AST:ALT ratio, the steatotest (alpha 2 Macroglobulin (A2M), Haptoglobin, apolipoprotein A1, Total Bilirubin, GGT, fasting blood gluose and adjustment for age, sex, weight and height), and the NAFLD ridge score (ALT, cholesterol, triglycerides, glycated hemoglobin A1c (HbA1c) and leukocyte count) and comorbidity data (hypertension).

In a particular embodiment, genetic and genomic markers may assess NAFLD risk and severity (Single Nucleotide Polymorphisms (SNPs):rs738409 (SNP in PNPLA3), cell-free non coding RNAs, miR-122, composite panel of serum derived omics data).

The present invention relates to a method for the diagnosis or detection of a NAFL in a subject, comprising determining the level of miR-452, in a body fluid sample of said subject.

The present invention also relates to a method for the diagnosis or detection of a potential NAFL in a subject, comprising determining the level of miR-452, in a body fluid sample of said subject. In a particular embodiment, NAFL or potential NAFL is detected based on increased level of miR-452 in the body fluid sample from the subject, relative to a reference level measured in a sample from a subject with no hepatic steatosis. In a further particular embodiment, the diagnosis or detection of NAFL or potential NAFL is based on the detection of an increased level of miR-452 in a body fluid sample relative to levels generally measured in healthy subjects with no hepatic steatosis. In a particular embodiment, the method further comprise a step of confirming that the subject suffers from NAFL. Such confirmation may be implemented according to any method known by those skilled in the art, such as by conducting a liver biopsy or by ultrasound or imaging techniques (such as ultrasonography, controlled attenuation parameter measurement by transient elastography (Fibroscan), Magnetic Resonance Imaging (MRI), MRI-estimated proton density fat fraction (MRI-DPFF), and the Magnetic resonance spectroscopy density fat fraction (MRS-DPFF)). Alternatively, several indices and scores may assess hepatic steatosis, including, without limitation:

the fatty liver index (FLI) which comprises BMI, waist circumference and serum levels of triglycerides and gamma glutaryl transferase (GGT), the hepatic steatosis index (HIS) which includes serum aspartate aminotransferase (AST): Alanine aminotransferase (ALT) ratio, BMI, gender and presence of diabetes mellitus, the NAFLD liver fat score (metabolic syndrome, type 2 diabetes, fasting serum insulin and AST, AST:ALT ratio, the steatotest (alpha 2 Macroglobulin (A2M), Haptoglobin, apolipoprotein A1, Total Bilirubin, GGT, fasting blood gluose and adjustment for age, sex, weight and height), and the NAFLD ridge score (ALT, cholesterol, triglycerides, glycated hemoglobin A1c (HbA1c) and leukocyte count) and comorbidity data (hypertension).

In a particular embodiment, genetic and genomic markers may assess NAFLD risk and severity (Single Nucleotide Polymorphisms (SNPs):rs738409 (SNP in PNPLA3), cell-free non coding RNAs, miR-122, composite panel of serum derived omics data).

The present invention also relates to a method for the diagnosis or detection of a NASH in a subject, comprising determining the level of miR-452, in a body fluid sample of said subject. The present invention also relates to a method for the diagnosis or detection of a potential NASH in a subject, comprising determining the level of miR-452, in a body fluid sample of said subject. In a particular embodiment, the diagnosis or detection of NASH or of potential NASH is based on the detection of an increased level of miR-452 in the body fluid from the subject, relative to a reference level of miR-452 measured in a healthy subject, in a subject with NAS<3 or in a subject with at least one component of NAS scored at 0. In a particular embodiment, the reference sample is from a subject with a NAS<3 with at least one component of NAS scored at 0, such as a subject with the following scores: S=1, LI=1 and HB=0; S=1, LI=0 and HB=1; S=0, LI=1 and HB=1. In a particular embodiment, the diagnosis or detection of NASH or potential NASH is based on the detection of an increased level of hsa-miR-452, particularly of hsa-miR-452-5p, and hsa-miR-452-3p, in blood, serum or plasma relative to reference levels measured in non-NASH subjects including healthy subjects, subjects with NAS<3 or subjects with at least one component of NAS scored at 0. In a particular embodiment, the method further comprises a step of confirming that the subject suffers from NASH. Such confirmation may be implemented according to any method known by those skilled in the art, such as by conducting a liver biopsy or by imaging biomarkers measured by imaging techniques such as MRI based techniques, gadoxetic acid used with MRI, super paramagnetic iron oxide MRI, P-MRS and MRE. Alternatively, several indices and scores Intracellular ATP level using 32P-MRS and MRE. Alternatively, several indices and scores may assess potential NASH biomarkers, including, without limitation:

apoptosis markers (CK18 fragment, total cytokeratin, serum levels of apoptosis-mediating surface antigen FAS), inflammatory markers (C-reactive protein (CRP), TNF, IL-8, CXC chemokine ligand 10 (CXCL10)), lipid oxidation products (11-hydroxyeicosatetraenoic acid (HETE), 9-hydroxydecadienoic acid (HODE), 13-HODE, 13-oxo-octadecadienoic acid (ODE), LA-13-HODE (oxNASH score), 11,12-dihydroxy-eicosatrienoic acid (diHETrE)), -adipocytokines and hormones (adiponectin, leptin, resistin, visfatin, retinol binding protein (RBP)4, fatty acid binding protein (FABP)4, fibroblast growth factor (FGF21)), lysosomal enzymes (cathepsin D), and -combined panels (NASH test, NASH diagnostic panel).

The present invention also relates to a method for the diagnosis or detection of Active-NASH in a subject, comprising determining the level of miR-452, in a body fluid sample of said subject. The present invention also relates to a method for the diagnosis or detection of a potential Active-NASH in a subject, comprising determining the level of miR-452, in a body fluid sample of said subject. In a particular embodiment, the diagnosis or detection of Active-NASH or of potential Active-NASH is based on the detection of an increased level of miR-452 in the body fluid from the subject, relative to a reference level of miR-452 measured in a healthy subject, in a subject with NAS<4 or in a subject with at least one component of NAS scored at 0. In a particular embodiment, the reference sample is from a subject with a NAS=3, with S=1, LI=1 and HB=1. In a particular embodiment, the diagnosis or detection of Active-NASH or potential Active-NASH is based on the detection of an elevated expression level of hsa-miR-452, particularly of hsa-miR-452-5p, and hsa-miR-452-3p, in blood, serum or plasma samples of a subject compared to reference levels measured in healthy subjects, subjects with NAS<4 or subjects with at least one component of NAS scored at 0. In a particular embodiment, the method further comprises a step of confirming that the subject suffers from Active-NASH. Such confirmation may be implemented according to any method known by those skilled in the art, such as by conducting a liver biopsy or by imaging techniques such as MRI based techniques, super paramagnetic iron oxide MRI, multiparametric MRI, MRS and MRE. Alternatively, several indices and scores may assess potential NASH biomarkers, including, without limitation:

apoptosis markers (CK18 fragment, total cytokeratin, serum levels of apoptosis-mediating surface antigen FAS), inflammatory markers (C-reactive protein (CRP), TNF, IL-8, CXC chemokine ligand 10 (CXCL10)), lipid oxidation products (11-hydroxyeicosatetraenoic acid (HETE), 9-hydroxydecadienoic acid (HODE), 13-HODE, 13-oxo-octadecadienoic acid (ODE), LA-13-HODE (oxNASH score), 11,12-dihydroxy-eicosatrienoic acid (diHETrE)), -adipocytokines and hormones (adiponectin, leptin, resistin, visfatin, retinol binding protein (RBP)4, fatty acid binding protein (FABP)4, fibroblast growth factor (FGF21)), lysosomal enzymes (cathepsin D), and -combined panels (NASH test, NASH diagnostic panel).

Such confirmation may be implemented by measuring NAFLD risk (progression towards NASH or Fibrosis) and severity markers like genetic and genomic markers like SNPs 20 (r5738409 in PNPLA3), cell-free non coding RNAs (miR-122, miR-1290, miR-192 and miR7b), composite panel of serum derived omics data like rs738409 and proteomic data including ACY1, SHBG, CTSZ, MET, GNS, LGALS3BP, CHL1 and SERPINC1, SNPs at multiple loci (PNPLA3, SOD2, KLF6 and LPIN1), miR-122, composite panel including miR-122, miR-192, miR-21, ALT, CK18 Asp396, cell free DNA like circulating methylated PPARG.

The present invention also relates to a method for characterizing the occurrence or grade of liver lobular inflammation in a subject, comprising determining the level of miR-452, in a body fluid sample of said subject.

The present invention also relates to a method for characterizing the occurrence or grade of hepatocyte ballooning in a subject, comprising determining the level of miR-452, in a body fluid sample of said subject.

The present invention also relates to a method for characterizing the occurrence or grade of liver steatosis in a subject, comprising determining the level of hsa-miR-452, in a body fluid sample of said subject.

The present invention also relates to a method for the diagnosis or detection of liver fibrosis in a subject, comprising determining the level of hsa-miR-452, in a body fluid sample of said subject. The present invention also relates to a method for the diagnosis or detection of a potential liver fibrosis in a subject, comprising determining the level of miR-452 in a body fluid sample of said subject. In a particular embodiment, the fibrosis is at minimum a significant fibrosis (i.e. F≥2). In a variant of this embodiment, the diagnosis or detection of liver fibrosis or of potential liver fibrosis is based on the detection of an increased level of miR-452 in the body fluid from the subject, relative to a reference level of miR-452 measured in a subject with no or minimal fibrosis, in particular with minimal fibrosis. In a further particular embodiment, the fibrosis is at minimum a moderate liver fibrosis or cirrhosis (i.e. F≥3). In a variant of this embodiment, the diagnosis or detection of liver fibrosis or of potential liver fibrosis is based on the detection of an increased level of miR-452 in the body fluid from the subject, relative to a reference level of miR-452 measured in a subject with no fibrosis, with minimal fibrosis, or with severe fibrosis, in particular with severe fibrosis. In a particular embodiment, the method further comprises a step of confirming that the subject suffers from liver fibrosis, or confirming the stage of liver fibrosis. Such confirmation may be implemented according to any method known by those skilled in the art, such as by conducting a liver biopsy or by imaging biomarkers, including, without limitation:

FibroScan (transient elastography),
Point shear wave elastography pSWE, acoustic radiation force impulse (ARFI)
2D 3D shear wave elastography 2D-3D SWE,
magnetic resonance elastography MRE,
multiparametric MRI.

Alternatively, several noninvasive tests of liver fibrosis and cirrhosis:

the AST:ALT ratio and the AST:platelet ratio index (APRI),
the fibrosis-4 index (FIB-4) which comprises age, AST, ALT, and platelet count
the NAFLD fibrosis score (age, BMI, impaired fasting glucose and/or diabetes, AST, ALT, platelet count, and albumin),
the BARD core (AST, ALT, BMI, and diabetes).

In another embodiment specific liver fibrosis markers and panel may assess liver fibrosis:

Specific fibrosis markers: Hyaluronic acid, N-terminal pro-peptide of collagen type III (PIIINP), neo epitope specific competitive enzyme linked immunosorbent assay for PIIINP (PRO-C3), Tissue Inhibitor Metalloproteinase 1 (TIMP-1), Laminin.

Specific fibrosis panels: Enhanced Liver Fibrosis (ELF) which includes PIIINP, Hyaluronic acid, and TIMP-1; Fibrotest (gamma glutamyl transferase (GGT), total bilirubin, alpha 2 macroglobulin (A2M), apolipoprotein A1 and haptoglobin; FibroMeter NAFLD (body weight, prothrombin index, ALT, AST, ferritin and fasting glucose).

The present invention also relates to a method for the determination of liver fibrosis stage in a subject, comprising determining the level of miR-452 (such as hsa-miR-452), in a body fluid sample of said subject.

In a particular embodiment, a F=4 stage may be determined if the level of miR-452 in the body fluid sample of said subject is higher than the level of miR-452 in a reference sample from a subject with a fibrosis stage F≤4, such as with F=0, F=1, F=2 or F=3. In a particular variant, the reference sample is from a subject with F=3.

In a particular embodiment, a F=3 stage may be determined if the level of miR-452 in the body fluid sample of said subject is higher than the level of miR-452 in a reference sample from a subject with a fibrosis stage F≤3, such as with F=0, F=1 or F=2. In a particular variant, the reference sample is from a subject with F=2.

In a particular embodiment, a F=2 stage may be determined if the level of miR-452 in the body fluid sample of said subject is higher than the level of miR-193 in a reference sample from a subject with a fibrosis stage F≤2, such as with F=0 or F=1. In a particular variant, the reference sample is from a subject with F=1.

In a particular embodiment, a F=1 stage may be determined if the level of miR-452 in the body fluid sample of said subject is higher than the level of miR-452 in a reference sample from a subject with a fibrosis stage F≤1, such as with F=0.

In a particular embodiment, the method is for the diagnosis and detection of significant to severe fibrosis (F≥2) and of advanced liver fibrosis (F≥3) in a subject with NAFLD or NASH, based on the detection of an elevated expression level of hsa-miR-452, particularly of hsa-miR-452-5p and hsa-miR-452-3p, in blood, serum or plasma samples of a subject compared to reference levels measured in patients with no and/or minimal fibrosis (F=0-1).

In a particular embodiment, the method for determining the stage of liver fibrosis further comprises a step of confirming the stage of liver fibrosis in the subject. Such confirmation may be implemented according to any method known by those skilled in the art, such as by conducting a liver biopsy or by other means like imaging biomarkers listed above for the diagnosis of fibrosis.

As liver fibrosis is a common consequence of most chronic liver diseases, the present invention also relates to diagnosis and detection of significant or advanced liver fibrosis due to other fibrotic liver diseases such as: viral hepatitis (HBV, HCV, . . . ), Alcoholic steatohepatitis, Biliary diseases (Primary biliary cholangitis, Primary Sclerosing cholangitis, Autoimmune hepatitis, Wilson's disease, Alpha1 antitrypsine deficiency).

The present invention also relates to a method for classifying a subject as a potential receiver or non-receiver treatment for NAFLD, NASH and/or liver fibrosis, comprising determining the level of miR-452, in a body fluid sample of said subject. In a particular embodiment, the method is for classifying the subject as a potential receiver or non-receiver treatment for NAFLD. In another particular embodiment, the method is for classifying the subject as a potential receiver or non-receiver treatment for NASH. In a further embodiment, the method is for classifying the subject as a potential receiver or non-receiver treatment for liver fibrosis.

The present invention also relates to a method for classifying a subject as a potential receiver or non-receiver treatment for NAFL, comprising determining the level of miR-452, in a body fluid sample of said subject. In a particular embodiment, the method is for classifying the subject as a potential receiver or non-receiver treatment for NAFL. In another particular embodiment, the method is for classifying the subject as a potential receiver or non-receiver treatment for NAFL. In a further embodiment, the method is for classifying the subject as a potential receiver or non-receiver treatment for liver fibrosis.

The present invention more particularly relates to a method for classifying a subject as a potential receiver (TBT) or non-receiver (NTBT) of a treatment for NASH and/or fibrosis, comprising determining the level of hsa-miR-452, in a body fluid sample of said subject.

In a particular embodiment, a subject is classified as a TBT2 subject if the level of miR-193 in the body fluid sample from said subject is higher than the level of miR-193 in a reference sample of a NTBT2 subject. In a specific variant, the NTBT2 subject is a subject with a NAS=4, S≥1, LI≥1, HB≥1 and F=1 (e.g. a 1a, 1b or 1c fibrosis stage).

In a particular embodiment, a subject is classified as a TBT1 subject if the level of miR-193 in the body fluid sample from said subject is higher than the level of miR-193 in a reference sample of a NTBT1 subject. In a specific variant, the NTBT1 subject is a subject with a NAS=4, S≥1, LI≥1, HB≥1 and F=0.

In a particular embodiment, a subject is classified as a TBT7 subject if the level of miR-193 in the body fluid sample from said subject is higher than the level of miR-193 in a reference sample of a NTBT7 subject. In a specific variant, the NTBT7 subject is a subject with a NAS=4, S≥1, LI≥1, HB≥1 and F=1a.

In a particular embodiment, the method of the invention is for classifying a subject as a TBT2 subject.

Other variants of the invention relates to a method for classifying patients as being potential receiver (TBT) or non-receiver (NTBT) of a treatment for NASH and/or fibrosis, based on the detection of an elevated expression level of hsa-miR-452, particularly of hsa-miR-452-5p and hsa-miR-452-3p, in blood, serum or plasma compared to reference levels of hsa-miR-452 measured in NTBT patients.

Such a classification may also be the basis for determining whether a subject should undergo further liver investigations, such as state-of-the-art liver investigations before taking decision to treat, such as ultrasound, elastography, imaging techniques including MRI, or liver biopsy.

The definition of TBT or receiver vs NTBT or non-receiver patient may vary depending on the drug efficacy to safety of drug with varying disease activity values (NAS or activity Index) and varying fibrosis stage value as provided above.

The present invention also relates to a method for the determination of a NAFLD or NASH activity in a subject, comprising determining the level of hsa-miR-452, in a body fluid sample of said subject.

The invention also relates to a method for the prognostic of the risk of NAFLD or NASH activity evolution in the absence of a treatment in a subject, comprising determining the level of hsa-miR-452, in a body fluid sample of said subject.

The present invention also relates to a method for the determination of liver fibrosis stage in a subject, comprising determining the level of hsa-miR-452, in a body fluid sample of said subject.

The invention also relates to a method for the prognostic of the risk of fibrosis evolution to cirrhosis and liver clinical outcomes in the absence of treatment in a subject, comprising determining the level of hsa-miR-452, in a body fluid sample of said subject. In a particular embodiment, the method is for the prognostic of the risk fibrosis evolution to cirrhosis and liver clinical outcomes in the absence of a treatment.

The invention also relates to a method for monitoring the evolution (i.e. progression or regression) of NAFLD or NASH activity in a subject, comprising determining the level of hsa-miR-452, in a body fluid sample of said subject.

The invention also relates to a method for monitoring the evolution (i.e. progression or regression) of liver fibrosis in a subject, comprising determining the level of hsa-miR-452, in a body fluid sample of said subject.

The invention also relates to a method for predicting the response of a patient to a specific treatment of NAFLD, NASH and/or liver fibrosis in a subject, comprising determining the level of hsa-miR-452, in a body fluid sample of said subject.

The invention also relates to a method for predicting the response of a patient to a specific treatment of NAFL in a subject, comprising determining the level of hsa-miR-452, in a body fluid sample of said subject.

Thus, the invention relates to a method for the diagnosis and detection of NAFLD in a subject, based on the detection of an increased level of miR-452 in a body fluid sample relative to levels generally measured in healthy subjects with no hepatic steatosis.

Thus, the invention relates to a method for the diagnosis and detection of NAFL in a subject, based on the detection of an increased level of miR-452 in a body fluid sample relative to levels generally measured in healthy subjects with no hepatic steatosis, no hepatic ballooning and no lobular inflammation.

According to a first variant, the invention relates to a method for the diagnosis and detection of NASH in a subject, based on the detection of an increased expression level of hsa-miR-452, particularly of hsa-miR-452-5p and hsa-miR-452-3p, in blood, serum or plasma relative to reference levels measured in non-NASH subjects including healthy subject, subjects with NAS<3 or subjects with at least one component of NAS scored at 0.

According to a second variant, the invention relates to a method for the diagnosis and detection of Active-NASH in a subject, based on the detection of an elevated expression level of hsa-miR-452, particularly of hsa-miR-452-5p and hsa-miR-452-3p, in blood, serum or plasma samples of a subject compared to reference levels measured in healthy subjects, subjects with NAS<4 or subjects with at least one component of NAS scored at 0.

According to a further variant a method for characterizing the occurrence and grade of steatosis in the subject, based on the detection of level of hsa-miR-452 and particularly of hsa-miR-452-5p, and hsa-miR-452-3p in a sample of blood, serum or plasma of a subject.

According to a further variant a method for characterizing the occurrence and grade of hepatocellular ballooning in the subject, based on the detection of level of hsa-miR-452 and particularly of hsa-miR-452-5p, and hsa-miR-452-3p in a sample of blood, serum or plasma of a subject.

According to a further variant, the invention relates to a method for characterizing the occurrence and grade of lobular inflammation in the subject, based on the detection of level of hsa-miR-452 and particularly of hsa-miR-452-5p and hsa-miR-452-3p in a sample of blood, serum or plasma of a subject.

In the practice of the present invention, cut-off concentrations of miR-452 may be calculated to help the decision-making by the person implementing the methods of the present invention. The expression "cut-off concentration" as used herein refers to a concentration of miR-193 above which a statistical prediction of a symptom or disease is made, and below which a statistical prediction of a lack of a disease or symptom is made. Such cut-off concentrations may be determined as follows for different scenarios.

A cut-off concentration for classifying a subject as a subject with a NAFLD (or potential NAFLD) or as a healthy subject without a NAFLD, S=0, can be determined by:
 i) measuring miR-452 concentration in body fluid samples from reference cohorts of subjects including both subjects with a NAFLD and healthy subjects without NAFLD,
 ii) applying a dedicated statistical analysis to the reference data set to determine an optimal cut-off concentration.

In particular, the state of the art statistical method ROC (Receiver Operating Characteristics) can be used to calculate the optimal cut-off concentration for discriminating NAFLD and healthy subjects in reference cohorts.

A cut-off concentration for classifying a subject as a subject with a NAFL (or potential NAFL) or as a healthy subject without a NAFL, S=0, can be determined by:
 i) measuring miR-452 concentration in body fluid samples from reference cohorts of subjects including both subjects with a NAFL and healthy subjects without NAFL,
 ii) applying a dedicated statistical analysis to the reference data set to determine an optimal cut-off concentration.

In particular, the state of art statistical method ROC (Receiver Operating Characteristics) can be used to calculate the optimal cut-off concentration for discriminating NAFL and healthy subjects in reference cohorts.

A cut-off concentration for classifying a subject as a subject with NASH (or potential NASH) or as a subject without NASH can be determined by:
 i) measuring miR-452 concentrations in body fluid samples of reference cohorts of subjects including both subjects with NASH and subjects without NASH,
 ii) applying a dedicated statistical analysis to the reference data set to determine an optimal cut-off concentration.

In particular, the state of art statistical method ROC (Receiver Operating Characteristics) can be used to calculate the optimal cut-off concentration for discriminating subjects with NASH (or potential NASH) and subject without NASH in reference cohorts.

A cut-off concentration for classifying a subject as a subject with an Active-NASH (or potential Active-NASH) or as a subject without an Active-NASH subject can be determined by:
 i) measuring miR-452 concentrations in body fluid samples of reference cohorts of subjects including both subjects with Active-NASH and subjects without Active-NASH,
 ii) applying a dedicated statistical analysis to the reference data set to determine an optimal cut-off concentration. In particular, the state of art statistical method ROC (Receiver Operating Characteristics) can be used to calculate the optimal cut-off concentration for discriminating patient with Active-NASH (or potential Active-NASH) and subjects without Active-NASH in reference cohorts.

A cut-off concentration for classifying a subject as a subject with significant liver fibrosis (F≥2) (or potential significant liver fibrosis) or as a subject with no or minimal fibrosis can be determined by:
 i) measuring miR-452 concentrations in body fluid samples of reference cohorts of subjects including both subjects with significant to severe liver fibrosis (F≥2) or advanced liver fibrosis (F≥3) and subjects with no or minimal fibrosis (F=0-1), ii) applying a dedicated statistical analysis to the reference data set to determine an optimal cut-off concentration. In particular, the state of art statistical method ROC (Receiver Operating Characteristics) can be used to calculate the optimal cut-off concentration for discriminating subjects with significant liver fibrosis (F≥2) or advanced liver fibrosis (F≥3) and subjects with no or minimal fibrosis (F=0-1) in reference cohorts.

A cut-off concentration for classifying a subject as a TBT subject or as a NTBT subject can be determined by:

i) measuring miR-452 concentrations in body fluid samples of reference cohorts of subjects including both TBT subjects and NTBT subjects, ii) applying a dedicated statistical analysis to the reference data set to determine an optimal cut-off concentration. In particular, the state of art statistical method, ROC (Receiver Operating Characteristics) can be used to calculate the optimal cut-off concentration for discriminating TBT subjects and NTBT in reference cohorts.

The data presented herein show that miR-452 is a circulating diagnostic biomarker for non-invasive grading of histological lesions (steatosis, lobular inflammation, hepatocyte ballooning), assessment of NAFLD activity level, NASH activity level and assessment of liver fibrosis severity in a subject.

According to another variant of the present invention, is provided a method to prognostic the risk of NAFLD or NASH activity evolution in a subject in the absence of a treatment, based on the level of miR-452 in a body fluid sample of a subject.

Another variant of the invention relates to a method to prognostic the risk of fibrosis evolution to cirrhosis and liver outcomes of a NAFLD or NASH patient based on the level of miR-452, measured in a body fluid sample of a subject. The present invention is also dedicated to prognostic the risk of fibrosis evolution in patients suffering from other fibrotic liver diseases such as: viral hepatitis (HBV, HCV, . . . ), Alcoholic steatohepatitis, Biliary diseases (Primary biliary cholangitis, Primary Sclerosing cholangitis, Autoimmune hepatitis, Wilson's disease, Alpha1 antitrypsine deficiency).

The inventors have also shown that there is a correlation between changes in circulating levels of miR-452 and evolution of histological scores, notably evolution of the Activity Index, NAS and fibrosis stage. These analyses support the use of miR-452 in a method for monitoring histological evolutions in a subject whether the subject is treated or not with an anti-NAFLD, anti-NASH drug or anti-fibrotic drug. Furthermore, the method of the invention can be used for assessing the anti-NAFLD, anti-NASH and/or anti-fibrotic activity of a drug in interventional trials assuming changes in serum level miR-452 as surrogates of histological evolutions.

Thus, another variant of the invention relates to a method for monitoring the evolution (i.e. progression or regression) of NAFLD or NASH activity based on the evolution of the level of miR-452 in body fluid samples collected two or more times apart from the same subject.

Another variant of the invention relates to a method for monitoring the evolution (i.e. progression or regression) of liver fibrosis stage based on the evolution of the level of miR-452 in body fluid samples collected two or more times apart from a same subject.

The present invention is also dedicated to the determination of fibrosis stage evolution in other fibrotic liver diseases such as: viral hepatitis (HBV, HCV,..), Alcoholic steatohepatitis, Biliary diseases (Primary biliary cholangitis, Primary Sclerosing cholangitis, Autoimmune hepatitis, Wilson's disease, Alpha1 antitrypsine deficiency).

Another variant of the invention relates to a method for predicting the response of a subject (prediction of changes in NAFLD activity, NASH activity and liver fibrosis stage) to a specific treatment (responder subject) based on the detection of a differential expression level of miR-452 in a body fluid sample of the subject compared to reference levels measured in non-responder subjects.

Thus, according the present invention, methods are provided to:
characterize the occurrence of NAFLD in a subject,
characterize the occurrence of NAFL in a subject,
characterize the occurrence of NASH in a subject,
characterize the occurrence of liver fibrosis in a subject,
characterize the occurrence of hepatocellular ballooning in a subject,
characterize the occurrence of lobular inflammation in a subject, or
characterize the occurrence of liver steatosis in a subject.

Furthermore, according to the present invention, methods are provided to:
diagnose the subject to have NAFLD and/or a more advanced NAFLD,
diagnose the subject to have NAFL and/or more advanced NAFL,
diagnose the subject to have NASH and/or a more advanced NASH,
diagnose the subject to have liver fibrosis and/or a more advanced liver fibrosis stage,
diagnose the subject to have hepatocellular ballooning and/or a more advanced hepatocellular ballooning score,
diagnose the subject to have lobular inflammation and/or more advanced lobular inflammation score, or
diagnose the subject to have liver steatosis and/or more advanced liver steatosis score.

Furthermore, the methods according to the present invention allow to:
determine the activity of a NAFLD or NASH in a subject,
determine the NAFL stage in a subject,
determine the fibrosis stage in a subject,
determine the severity of a NASH in a subject, or
determine the progression or regression of the pathology in a NASH patient, Furthermore, the methods according to the present invention allow to:
classify a subject as a receiver or non-receiver of a treatment for NAFLD,
classify a subject as a receiver or non-receiver of a treatment for NASH,
classify a subject as a receiver or non-receiver of a treatment for liver fibrosis,
classify a subject as a receiver or non-receiver of a treatment for hepatocellular ballooning,
classify a subject as a receiver or non-receiver of a treatment for lobular inflammation, or
classify a subject as a receiver or non-receiver of a treatment for liver steatosis.

Furthermore, the methods according to the present invention allow to:
assess the efficacy of a medical treatment based on a drug administration to treat NAFLD disease,
assess the efficacy of a medical treatment based on a drug administration to treat NAFL.

assess the efficacy of a medical treatment based on a drug administration to treat NASH disease,
assess the efficacy of a medical treatment based on a drug administration to treat fibrosis disease,
assess the efficacy of a medical treatment based on a drug administration to treat hepatocellular ballooning disease,
assess the efficacy of a medical treatment based on a drug administration to treat lobular inflammation disease, or
assess the efficacy of a medical treatment based on a drug administration to treat liver steatosis.

Furthermore, the methods according to the present invention allow to:
determine the progression or regression of the pathology in a NAFLD patient after the administration of a medical treatment,
determine the progression or regression of the pathology in a NAFL patient after the administration of a medical treatment,
determine the progression or regression of the pathology in a NASH patient after the administration of a medical treatment,
determine the progression or regression of the pathology in a patient suffering from fibrosis after the administration of a medical treatment,
determine the progression or regression of the pathology in a patient suffering from hepatocellular ballooning disease after the administration of a medical treatment, or
determine the progression or regression of the pathology in a patient suffering from lobular inflammation disease after the administration of a medical treatment.

Furthermore, the methods according to the present invention allow to:
predict if a patient will responds or not, -i.e. potential responder or non-responder to a particular medical treatment to treat NAFLD,
predict if a patient will responds or not, -i.e. potential responder or non-responder to a particular medical treatment to treat NAFL,
predict if a patient will be receptive or not, i.e. (potentially) responder or (potentially) non-responder to a medical treatment to treat NASH disease,
predict if a patient will be receptive or not, i.e. (potentially) responder or (potentially) non-responder to a medical treatment to treat liver fibrosis,
predict if a patient will be receptive or not, i.e. (potentially) responder or (potentially) non-responder to a medical treatment to treat a hepatocellular disease, or
predict if a patient will be receptive or not, i.e. (potentially) responder or (potentially) non-responder to a medical treatment to treat a lobular inflammation disease.

In some embodiments, the methods for determining whether a subject has NAFLD or NASH, or Active-NASH or liver fibrosis (such as significant liver fibrosis), or lobular inflammation, or hepatocyte ballooning or for determining if a subject is a drug receiver (TBT) or a potential responder to a specific drug comprise collecting a sample of a body fluid from a subject suspected of having the assessed condition, and detecting the level of miR-452 wherein a level that is higher than a reference level of miR-452 indicates the presence of the assessed condition, or the diagnosis of the subject as having NAFLD or NASH, or Active-NASH or liver fibrosis (such as significant liver fibrosis), or lobular inflammation, or hepatocyte ballooning or the subject as being a potential drug receiver (TBT) or responder.

In particular embodiments, the subject is a subject at risk of having NALFD, NASH, Active-NASH or liver fibrosis or a subject at risk of developing NAFLD, NASH, Active-NASH or liver fibrosis in the future, such as a subject having obesity, diabetes, suffering from the metabolic syndrome, and/or having elevated liver enzymes and/or having other signs of liver dysfunctions. The subject may also be a subject with previously identified NAFLD, NASH or Active-NASH or liver fibrosis, the method of the invention thereby allowing determining the disease activity and fibrosis stage and estimating risks of evolution of the disease towards cirrhosis, cirrhotic complications, hepatocarcinoma, liver transplantation, a cardiovascular disease or liver-related deaths.

In particular embodiments, the subject is suffering from NASH, the method of the invention thereby allowing determining the efficacy of a drug for the treatment of the NASH disease, classifying the subject as responder/non-responder to a treatment for NASH, or monitoring the evolution of the NASH state of the subject.

In particular embodiments of the present invention for diagnosing NAFLD, NASH or liver fibrosis and/or for determining the disease activity, the fibrosis stage, in a subject, and/or for the evaluation of the efficacy of a medical treatment, and/or for the determination of the evolution (progression or regression) of the pathology in a NAFLD, NASH or liver fibrosis subject, and/or for the classification of a subject as a potential responder or non-responder to a medical treatment, and/or for the prediction of disease outcome for a subject, the measure of miR-452 level can be introduced in mathematical models (algorithms) for combination with other variables such as sex, age, body mass index, weight, medical status, arterial pressure or other body fluid markers such as blood, serum or plasma circulating markers, notably those mentioned in the following table.

| Hepatocyte function | Adipose tissue | Metabolism | Oxidative stress/apoptosis | Fibrosis | Inflammation |
| --- | --- | --- | --- | --- | --- |
| ALT | Adiponectin | Fasting plasma glucose | Malondialdehyde | Fibronectin | TNFa |
| AST | Leptin | Fasting insulin | TBARS | Hyaluronic acid | IL1b, IL6, IL8, IFNg, TGFb |
| ALP | Resistin | HOMA index | Ox LDL | Type IV collagen | hs -CRP |
| GGT | | Trglycerides | CK18-M30 | PIIINP | MCP1 |
| Haptoglobin | | HDL-Cholesterol | CK18-M65 | TIMP-1 | sCD14 |
| Albumin | | VLCL-C | Ferritin | | |
| Bilirubin | | Apolipoproteins (ApoA1, ApoB, ApoCIII) | YKL-40 (CHI3L1) | | |
| Platelet Count | | | | | |

According to another embodiment, the methods of the present invention comprise the determination of the level of other biomarkers in addition to miR-452.

In a particular embodiment such biomarkers are selected from the group consisting of: alpha 2 macroglobulin (A2M), glycated haemoglobin (HbA1c), fasting glucose level or fructosamine level, N-terminal pro-peptide of collagen type III (PIIINP) and YKL-40.

In a more particular embodiment such biomarker is YKL-40.

In another embodiment, such biomarkers are NAFLD, NASH or liver fibrosis markers, such as the degree of steatosis, necroinflammation and fibrosis, estimated by Magnetic Resonance Imagery (MRI), Magnetic Resonance Elastography (MRE), Magnetic Resonance Spectroscopy (MRS), Controlled attenuation parameter (CAP) and liver stiffness measurement by Transient Elastography (TE), Ultrasonography (USG), FibroScan, Point Shear Wave Elastography (pSWE), 2D Shear Wave Elastography (2D-SWE), Single Nucleotide Polymorphisms (SNP), cell free DNA, cell free non coding RNA, and gene polymorphisms (such as PNPLA3 and TM6SF2).

In a particular embodiment, such biomarkers are NAFLD markers like fatty liver index related markers, Hepatic steatosis index related markers, NAFLD liver fat score related markers, SteatoTest parameters, NAFLD ridge score parameters, circulating triglycerides, Body Mass Index (BMI); imaging biomarkers like the degree of beam scattering by the tissue (USG), the degree of ultrasound attenuation by hepatic fat (CAP), the proton density fat fraction (MRI-PDFF), the liver triglyceride content, signal fat fraction (MRS).

In a particular embodiment, such biomarkers are NASH biochemical blood markers like apoptosis markers (CK18 fragment, total cytokeratin, serum levels of apoptosis-mediating surface antigen FAS), inflammatory markers (C-reactive protein (CRP), TNF, IL-8, CXC chemokine ligand 10 (CXCL10)), lipid oxidation products (11-hydroxyeicosatetraenoic acid (HETE), 9-hydroxydecadienoic acid (HODE), 13-HODE, 13-oxo-octadecadienoic acid (ODE), LA-13-HODE (oxNASH score), 11,12-dihydroxy-eicosatrienoic acid (diHETrE)), adipocytokines and hormones (adiponectin, leptin, resistin, visfatin, retinol binding protein (RBP)4, fatty acid binding protein (FABP)4, fibroblast growth factor (FGF21)), lysosomal enzymes (cathepsin D), and/or combined panels (NASH test, NASH diagnostic panel); imaging biomarkers like kupffer cell uptake function (MRI), increased liver enhancement by the use of gadoxetic acid (MRI), hepatocyte membrane turnover and intracellular ATP (MRS), liver stiffness (MRE).

In a particular embodiment, such biomarkers are liver fibrosis markers: imaging biomarkers like mechanically induced impulse, quantitative measurement of shear wave speed (FibroScan-transient elastography, pSWE-ARFI, 2D-3D-SWE), ultrasound induced focused radiation force impulse at death (pSWE-ARFI), use of modified phase-contrast method to image the propagation of the shear wave in liver parenchyma (MRE); biochemical bloodmarkers like the AST:ALT ratio, the AST:platelet ratio index (APRI), the FIB4 index parameters, the NAFLD fibrosis score parameters, the BARD score parameters, specific fibrosis markers like HA, PIIINP, Pro-C3, TIMP-1, Laminin, ELF related panels, fibrotest parameters, fibroMeter NAFLD parameters.

In another further embodiment such markers are NAFLD risk and severity markers like genetic and genomic markers like SNPs (r5738409 in PNPLA3), cell-free non coding RNAs (miR-122, miR-1290, miR-192 and miR-7b), composite panel of serum derived omics data like rs738409 and proteomic data including ACY1, SHBG, CTSZ, MET, GNS, LGALS3BP, CHL1 and SERPINC1, SNPs at multiple loci (PNPLA3, SOD2, KLF6 and LPIN1), miR-122, composite panel including miR-122, miR-192, miR-21, ALT, CK18 Asp396, cell free DNA like circulating methylated PPARG.

According to a further embodiment, the other biomarkers are other circulating microRNAs in addition to miR-452. In particular, illustrative additional microRNAs that may be useful in the practice of the present invention include: miR-34a, miR-122 and miR-200.

According to these embodiments, the methods may comprise the steps of:

i) measuring the level of miR-452 and at least one other circulating marker of liver damage (such as a blood, serum or plasma circulating marker of liver damage), and ii) combining these measures for generating mathematical models (algorithms) through bioinformatic approaches (for example, linear logistic regression or random forest) for obtaining a NAFLD, NASH and/or liver fibrosis score with high diagnostic/monitoring/prognostic/predictive performances for assessment of NALFD, NASH, Active-NASH or liver fibrosis in a subject.

In another embodiment, the diagnosis, detection, monitoring, evaluation of the risk or evaluation of the efficacy of a treatment for NAFLD, NASH or liver fibrosis is conducted by determining the level of miR-452 in a body fluid sample of the subject, and submitting the subject to physical, non-invasive, techniques such as ultrasound, elastography or imaging techniques such as MRI.

In other embodiments, the methods of the present invention may be combined to the method disclosed in WO2017046181 owned by the same Applicant.

In some embodiments, thanks to the methods of the invention, a decision may be taken to give life style recommendations to a subject (such as a food regimen or providing physical activity recommendations), to medically take care of a subject (e.g. by setting regular visits to a physician or regular examinations, for example for regularly monitoring markers of liver damage), or to administer at least one NAFLD, NASH or liver fibrosis therapy to a subject. In a particular embodiment, a decision may be taken to give life style recommendations to a subject or to administer at least one NAFLD, NASH or liver fibrosis therapy. Such a classification of a subject as a receiver or TBT patient is based on an elevated level on miR-452 compared to reference miR-452 levels measured in non-receiver patients (NTBT), as provided above.

The invention thus further relates to an anti-NAFLD, anti-NASH or anti-fibrotic compound for use in a method for treating NAFLD, NASH or liver fibrosis in a subject in need thereof, wherein the subject has been identified thanks to a method according to the invention. The invention also further relates to an anti-NAFL compound for use in a method for treating NAFL in a subject in need thereof, wherein the subject has been identified thanks to a method according to the invention.

In particular, the invention relates to an anti-NAFLD compound for use in a method for treating NAFLD in a subject in need thereof, wherein the subject has been classified as a receiver of said treatment thanks to a method according to the invention.

In particular, the invention relates to an anti-NASH compound for use in a method for treating NASH in a subject in need thereof, wherein the subject has been classified as a receiver of said treatment thanks to a method according to the invention.

In particular, the invention relates to an anti-fibrotic compound for use in a method for treating liver fibrosis in a subject in need thereof, wherein the subject has been classified as a receiver of said treatment thanks to a method according to the invention.

Illustrative anti-NAFLD anti-NASH and anti-fibrotic compounds are listed below:

a compound of formula (I):

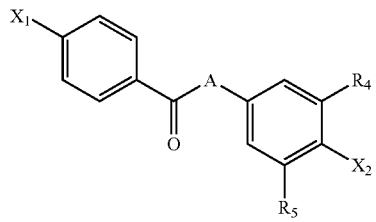

wherein:
X1 represents a halogen, a R1, or G1—R1 group;
A represents a CH═CH or a CH2—CH2 group;
X2 represents a G2—R2 group;
G1 and G2, identical or different, represent an atom of oxygen or sulfur;
R1 represents a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 represents an alkyl group substituted by at least a —COOR3 group, wherein R3 represents a hydrogen atom, or an alkyl group that is substituted or not by one or more halogen atoms, cycloalkyl groups, or heterocyclic groups.
R4 and R5, identical or different, representing an alkyl group that is substituted or not by one or more halogen atoms, cycloalkyl groups, heterocyclic groups;
or a pharmaceutically acceptable salt thereof;

Acetyl-CoA carboxylase inhibitors like GS-0976, ND-654, AC-8632, PF05175157, CP640186, gemcabene, MK-4074, and PF05175157.

Adenosine A3 receptor agonists like 2-(1-Hexynyl)-N-methyladenosine, Piclidenoson CF101 (IB-MECA), Namodenoson CF-102, 2-CI-IB-MECA, CP-532,903, Inosine, LUF-6000, and MRS-3558.

Aldosterone antagonists and mineralocorticoid receptor antagonists like Apararenone (MT 3995), Amiloride, Spironolactone, Eplerenone, Canrenone and potassium canrenoate, progesterone, drospirenone, gestodene, and benidipine.

AMP activated protein kinase stimulators like PXL-770, MB-11055 Debio-0930B metformin, CNX-012, O-304, mangiferin calcium salt, eltrombopag, carotuximab, and Imeglimin.

Amylin receptor agonist and Calcitonin receptor agonists include, but are not limited to, KBP-042 and KBP-089.

Antisense oligonucleotide targeting transforming growth factor beta 2 include, but are not limited to ASPH-0047, IMC-TR1 and ISTH-0047.

Angiopoietin-related protein-3 inhibitors like ARO-ANG3, IONIS-ANGGPTL3-LRx or AKCEA-ANGPTL3LRx, evinacumab, and ALN-ANG.

Anti-LPS antibodies like IMM-124-E

Apical sodium-codependent bile acid transporter inhibitors like A-4250, volixibat, maralixibat formerly SHP-625, GSK-2330672, elobixibat, and CJ-14199.

Betaine anhydrous or RM-003;

Bile acids like obeticholic acid (OCA) and UDCA, norursodeoxycholic acid, and ursodiol.

Bioactive lipids like 5-hydroxyeicosapentaenoic acid (15-HEPE, DS-102), unsaturated fatty acids such as 25 arachidonic acid, icosapentethyl ester, eicosapentaneoic acid, and docosahexaenoic acid.

Cannabinoid CB1 receptor antagonists like GRC-10801, MRI-1569, MRI-1867, DBPR-211, AM-6527: AM-6545, NESS-11-SM, CXB-029, GCC-2680, TM-38837, Org-50189, PF-514273, BMS-812204, ZYO-1, AZD-2207, AZD-1175, otenabant, ibipinabant, surinabant, rimonabant, drinabant, SLV-326, V-24343, and O-2093.

Cannabinoid CB2 receptor mimetics like anabasum (Resunab, JKT-101).

Dual cannabinoid CB1 receptor/iNOS inhibitor

Caspase inhibitors like emricasan, belnacasan, nivocasan, IDN-7314, F-573, VX-166, YJP-60107, MX-1122, IDN-6734, TLC-144, SB-234470, IDN-1965, VX-799, SDZ-220-976, and L-709049.

Cathepsin inhibitors like VBY-376, VBY-825, VBY-036, VBY-129, VBY-285, Org-219517, LY3000328, RG-7236, and BF/PC-18.

CCR antagonists like cenicriviroc (CCR2/5 antagonist), PG-092, RAP-310, INCB-10820, RAP-103, PF-04634817, and CCX-872.

CCR3 chemokine modulators and eotaxin 2 ligand inhibitors.

Diacylglycerol-O-acyltransferase (DGAT) inhibitors like IONIS-DGAT2Rx formerly ISIS-DGAT2Rx, LY-3202328, BH-03004, KR-69530, OT-13540, AZD-7687, ABT-046.

Dipeptidyl peptidase IV (DPP4) inhibitors like evogliptin, vidagliptin, fotagliptin, alogliptin, saxagliptin, tilogliptin, anagliptin, sitagliptin, retagliptin, melogliptin, gosogliptin, trelagliptin, teneligliptin, dutogliptin, linagliptin, gemigliptin, yogliptin, betagliptin, imigliptin, omarigliptin, vidagliptin, and denagliptin.

Insulin ligand and insulin receptor agonists.

Insulin sensitizer and MCH receptor-1 antagonis

Dual NOX (NADPH oxidase) 1&4 inhibitors like GKT-831 (2-(2-chlorophenyl)-4-[3-(dimethylamino)phenyl]-5-methyl-1H-pyrazolo[4,3- c]pyridine-3,6(2H, 5H)-dione), formerly GKT137831, and GKT-901.

Extracellular matrix protein modulators like CNX-024, CNX-025, and SB-030.

Stearoyl CoA desaturase-1 inhibitors/fatty acid bile acid conjugates (FABAC);

Farnesoid X receptor (FXR) agonists like obeticholic acid (OCA), GS-9674, LJN-452, EDP-305, AKN-083, INT-767, GNF-5120, LY2562175, INV-33, NTX-023-1, EP-024297, Px-103, and SR-45023.

Fatty acids like omega-3 fatty acids, Omacor or MF4637, fish oils, poly unsaturated fatty acids (efamax, optiEPA).

Fatty Acid Synthase (FAS) inhibitors like TVB-2640; TVB-3199, TVB-3693BZL-101, 2-octadecynoic acid, MDX-2, Fasnall, MT-061, G28UCM, MG-28, HS-160, GSK-2194069, KD-023, and cilostazol.

In a particular embodiment, the FAS inhibitor is a compound selected in the following list of compounds:

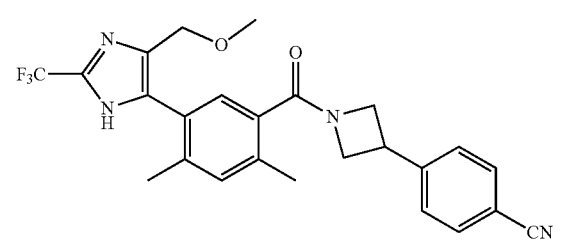
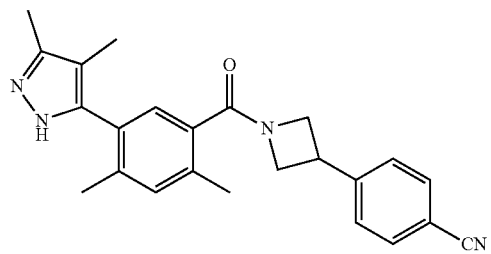
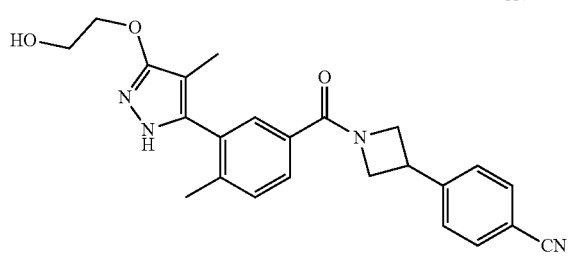
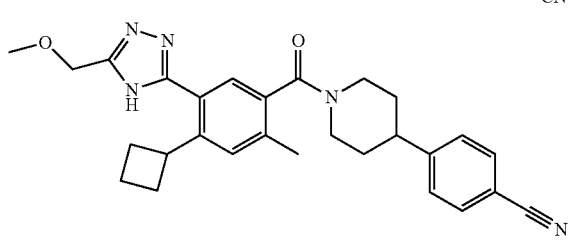
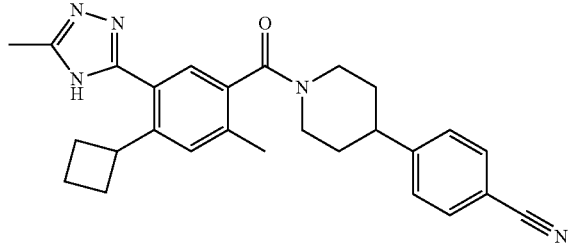
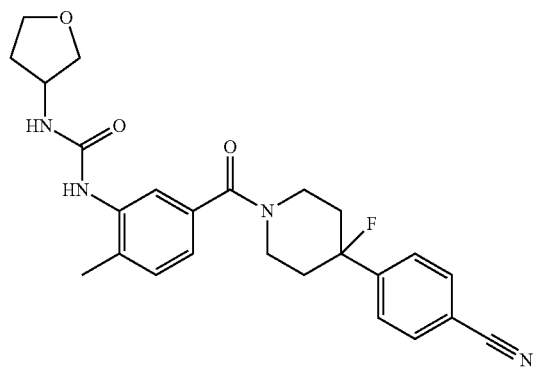
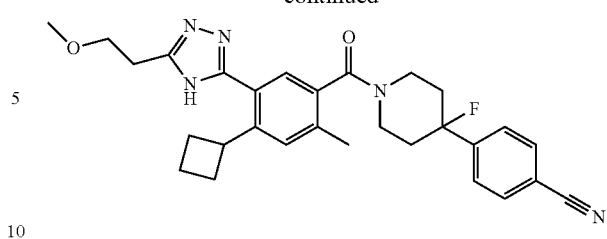
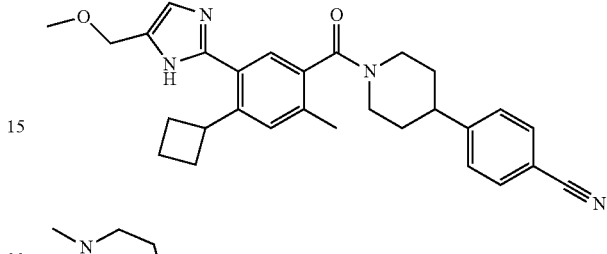
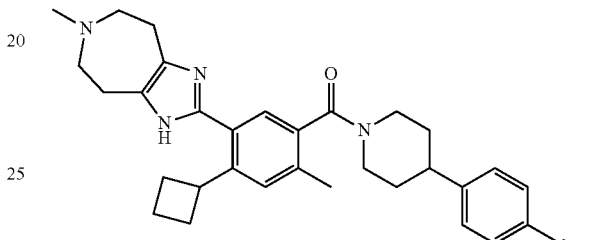
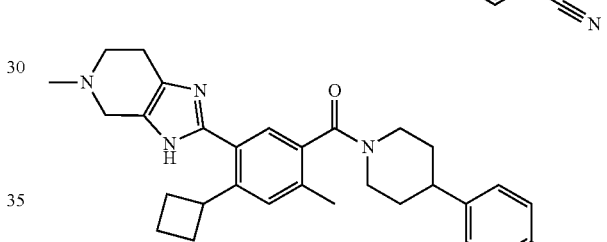
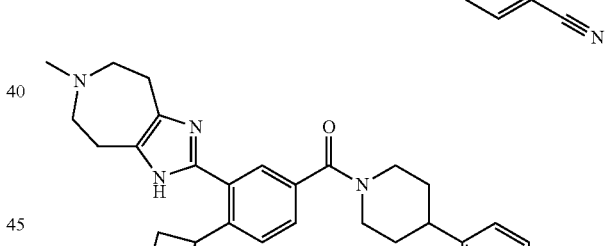
and TVB-2640.
In another particular embodiment, the FAS inhibitor is selected from:
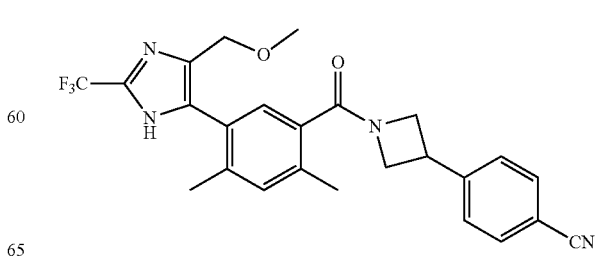

and TVB-2640.

In a particular embodiment, the FAS inhibitor is TVB-2640.

Fibroblast Growth Factor 19 (FGF-19) receptor ligand or functional engineered variant of FGF-19

Fibroblast Growth Factor 19 (FGF-19) recombinants like NGM-282

Fibroblast Growth Factor 21 (FGF-21) agonists like PEG-FGF21 formerly BMS-986036, YH-25348, BMS-986171, YH-25723, LY-3025876, and NNC-0194-0499.

Galectin 3 inhibitors like GR-MD-02, TD-139, ANG-4021, Galectin-3C, LJPC-201, TFD-100, GR-MD-03, GR-MD-04, GM-MD-01, GM-CT-01, GM-CT-02, Gal-100, and Gal-200.

Glucagon-like peptide-1 (GLP-1) analogs like semaglutide, liraglutide, exenatide, albiglutide, dulaglutide, lixisenatide, loxenatide, efpeglenatide, taspoglutide, MKC-253, DLP-205, ORMD-0901.

Glucagon-like peptide-1 (GLP-1) receptor agonists like LY-3305677, and Oxyntomodulin long acting.

G-protein coupled receptor (GPCR) modulators; CNX-023.

G-protein coupled receptor 84 antagonist (GPR84 antagonist), connective tissue growth factor ligand inhibitor and Free fatty acid receptor 1 agonist (FFAR1 agonist) like PBI-4050, PBI-4265, PBI-4283, and PBI-4299.

Growth hormone

Hedgehog cell-signalling pathway inhibitors like Vismodegib, TAK-441, IPI-926, Saridegib, Sonidegib/Erismodegib, BMS-833923/XL139, PF-04449913, Taladegib/LY2940680, ETS-2400, SHR-1539, and CUR61414.

Ileal sodium bile acid cotransporter inhibitors like A-4250, GSK-2330672, volixibat, CJ-15 14199, and elobixibat.

Immunomodulators like PBI-4050, PBI-4265, PBI-4283, PBI-4299 and AIC-649.

Insulin sensitizer and MCH receptor-1 antagonist like MSDC-0602k, MSDC-0602, CSTI-100 and AMRI.

Integrin inhibitors; integrin inhibitors of Pliant Therapeutic, integrin inhibitors of Indalo Therapeutics, integrin inhibitors of St Louis University, ProAgio, and GSK-3008348.

Ketohexokinase inhibitors like JNJ-28165722, JNJ-42065426; JNJ-42152981, JNJ-42740815, JNJ-42740828, and PF-06835919.

Leukotriene (LT)/Phosphodiesterase (PDE)/Lipoxygenase (LO) inhibitors like tipelukast (formerly MN-001), tomelukast, sulukast, masilukast, zafirlukast, pranlukast, montelukast, gemilukast, verlukast, aklukast, pobilikast, cinalukast, and iralukast.

Lysyl oxidase homolog 2 inhibitors like Rappaport, InterMune, Pharmaxis, AB-0023, Simtuzumab, PXS-5382A, and PXS-5338.

Macrolides: solithromycin, azithromycin, and erythromycin.

Macrophage mannose receptor modulators like AB-0023, MT-1001, [18F]FB18mHSA, Xemys, technetium Tc 99m tilmanocept, and CDX-1307.

Methyl CpG binding protein 2 modulator and transglutaminase inhibitors include, but are not limited to, cysteamine, EC Cysteamine, enteric-coated cysteamine bitartrate, cysteamine bitartrate (enteric-coated), Bennu, cysteamine bitartrate (enteric-coated), Raptor, cysteamine bitartrate, DR Cysteamine, delayed release enteric coated cysteamine bitartrate, mercaptamine, mercaptamine (enteric-coated), Bennu, mercaptamine (enteric-coated), Raptor, RP-103, RP-104, PROCYSBI, and mercaptamine (enteric-coated).

miRNA antagonists like RG-125 formerly AZD4076, RGLS-5040, RG-101, MGN-5804, and MRG-201.

Metalloproteinase 9 (MMP9) stimulator like MMP9 stimulator of Elastomic Ab.

Mitochondrial carrier family inhibitor and Mitochondrial phosphate carrier protein inhibitor include, but are not limited to TRO-19622, Trophos, olesoxime, RG-6083, or RO-7090919.

Myeloperoxidase inhibitors include, but are not limited to PF-06667272

Monoclonal antibodies: bertilimumab, NGM-313, IL-20 targeting mAbs, fresolimumab (antiTGFβ) formerly GC1008, timolumab formerly BTT-1023, namacizumab, omalizumab, ranibizumab, bevacizumab, lebrikizumab, epratuzumab, felvizumab, matuzumab, monalizumab, reslizumab, and inebilizumab.

Monoclonal antibodies like anti-IL20 mAbs, anti-TGFβ antibodies, anti-CD3 antibodies, anti-LOXL2 antibodies and anti-TNF antibodies.

mTOR modulators like MSDC-0602, AAV gene therapy co-administered with SVP-sirolimus.

NAD-dependent deacetylase sirtuin stimulator, PDE 5 inhibitor like NS-0200.

NF-kappa B inhibitors like LC-280126.

Nicotinic acid like Niacin or Vitamine B3

Nicotinic Acid Receptor (GPR109) Agonists like ARI-3037M0, MMF, LUF 6283, Acifran, IBC 293, MK-1903, GSK256073, MK-6892, MK-0354, SLx-4090, lomitapide, lexibulin, apabetalone, acifran, laropiprant, daporinad, anacetrapib, INCB-19602, ST-07-02, Iomefloxacin, Niacin, and controlled release/laropiprant, nitazoxanide (NTZ), its active metabolite tizoxanide (TZ) or other prodrugs of TZ such as RM-5061, non-steroid anti-inflammatory drugs (NSAIDs) include, but are not limited to F-351, salicylates (aspirin), acetaminophen, propionic acid derivatives (ibuprofen, naproxen), acetic acid derivatives (indomethacin, diclofenac), enolic acid derivatives (piroxicam, phenylbutazone), anthranilic acid derivatives (meclofenalmic acid, flufenamic acid), selective 25 COX-2 inhibitors (celecoxib, parecoxib), and sulfonanilides (nimesulide).

nuclear receptor ligands like DUR-928 formerly DV 928.

P2Y13 protein agonists like CER-209

PDGFR modulators like BOT-501 and BOT-191.

Phenylalanine hydroxylase stimulators like Pegvaliase, sapropterin, AAV-PAH, CDX-6114, sepiapterin, RMN-168, ALTU-236, ETX-101, HepaStem, rolipram, and alprostadil Protease-activated receptor (PAR)-2 antagonists; PZ-235, and NP-003.

Protein kinase modulators like CNX-014, MB-11055, ALF-1, mangiferin, amlexanox, GS-444217, REG-101, and valine.

PPAR alpha agonists like fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, and SR10171;

PPAR gamma agonists like Pioglitazone, deuterated pioglitazone, Rosiglitazone, efatutazone, ATx08-001, OMS-405, CHS-131, THR-0921, SER-150-DN, KDT-501, GED-0507-34-Levo, CLC-3001, and ALL-4.

PPAR delta agonists like GW501516 (Endurabol or ({4-[({4-methyl-2-[4-(trifluoromethyl)phenyl]-1,3-thiazol-5-yl}methyl)sulfanyl]-2-methylphenoxy}acetic acid)) or MBX8025 (Seladelpar or {2-methyl-4-[5-methyl-2-(4-trifluoromethyl-phenyl)-2H-[1,2,3]triazol-4-ylmethylsylfanyl]-phenoxy}-acetic acid) or GW0742 ([4-[[[2-[3-fluoro-4-(trifluoromethyl)phenyl]-4-methyl-5-thiazolyl]methyl]thio]-2-methyl phenoxy]acetic acid) or L165041 or HPP-593 or NCP-1046.

PPARalpha/gamma agonists (also named glitazars), like Saroglitazar, Aleglitazar, Muraglitazar, Tesaglitazar, and DSP-8658.

PPARalpha/delta agonists like Elafibranor, and T913659.

PPAR gamma/delta like conjugated linoleic acid (CLA), T3D-959.

PPAR alpha/gamma/delta agonists or PPARpan agonists: IVA337 or TTA (tetradecylthioacetic acid) or Bavachinin or GW4148 or GW9135, or Bezafibrate or Lobeglitazone, or CS038.

Prebiotic fibers, probiotics

Pregnane X receptors like Rifampicin.

Rho-associated protein kinase 2 (ROCK2) inhibitors: KD-025, TRX-101, BA-1049, LYC-53976, INS-117548, and RKI-1447.

signal-regulating kinase 1 (ASK1) inhibitors; GS-4997

Sodium-glucose transport (SGLT) 2 inhibitors: remogliflozin, dapagliflozin, empagliflozin, ertugliflozin, sotagliflozin, ipragliflozin, tianagliflozin, canagliflozin, tofogliflozin, janagliflozin, bexagliflozin, luseogliflozin, sergliflozin, HEC-44616, AST-1935, and PLD-101.

stearoyl CoA desaturase-1 inhibitors/fatty acid bile acid conjugates: aramchol, GRC-9332, steamchol, TSN-2998, GSK-1940029, and XEN-801.

thyroid receptor β (THR β) agonists: VK-2809, MGL-3196, MGL-3745, SKL-14763, sobetirome, BCT-304, ZYT-1, MB-07811, and eprotirome.

Toll Like Receptor 4 (TLR-4) antagonists like naltrexone, JKB-121, M-62812, resatorvid, dendrophilin, CS-4771, AyuV-1, AyuV-25, NI-0101, EDA-HPVE7, and eritoran.

Tyrosine kinase receptor (RTK) modulators; CNX-025; KBP-7018

Urate anion exchanger 1 inhibitors and xanthine oxidase inhibitors like lesinurad, RLBN-1001, verinurad, KUX-1151, and lesinurad+allopurinol.

Vascular adhesion protein-1 (VAP-1) inhibitors like PXS-4728A, CP-664511, PRX-167700, ASP-8232, RTU-1096, RTU-007, and BTT-1023.

Vitamin D receptor (VDR) agonists like calciferol, alfacalcidol, 1,25-dihydroxyvitamin D3, Vitamin D2, Vitamin D3, calcitriol, Vitamin D4, Vitamin D5, dihydrotachysterol, calcipotriol; tacalcitol 1,24-dihydroxyvitamin D3, and paricalcitol.

Vitamin E and isoforms, vitamin E combined with vitamin C and atorvastatin.

Other anti-NASH agents include KB-GE-001 and NGM-386 and NGM-395 and NC-10 and TCM-606F. Further anti-NASH agents include icosabutate, NC-101, NAIA-101 colesevelam, and PRC-4016. Other anti-fibrotic agents include HEC-585, INV-240, RNAi therapeutic (Silence Therapeutics) and SAMiRNA program (Bioneer Corp).

Other illustrative antifibrotic agents include pirfenidone or receptor tyrosine kinase inhibitors (RTKIs) such as Nintedanib, Sorafenib and other RTKIs, or angiotensin II (AT1) receptor blockers, or CTGF inhibitor, or any antifibrotic compound susceptible to interfere with the TGFβ and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canonical and non-canonical Hedgehog signaling pathways including Hh ligands or target genes, or any members of the WNT, or Notch pathways which are susceptible to influence TGFβ.

In a particular embodiment of the treatment of NASH or liver fibrosis comprises administering a compound of formula (I) selected in the group consisting of 1-[4-methylthiophenyl]-3-[3,5-dimethyl-4-carboxydimethylmethyloxy phenyl]prop-2-en-1-one, 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl]prop-2-en-1-one, 1-[4-trifluoromethylphenyl]-3-[3,5-dimethyl-4-tertbutyloxycarbonyl dimethyl methyloxyphenyl]prop-2-en-1-one, 1-[4-trifluoromethylphenyl]-3-[3,5-dimethyl-4-carboxydimethylmethyloxyphenyl]prop-2-en-1- one, 1-[4-trifluoromethyl oxyphenyl]-3-[3,5-dimethyl-4-tertbutyloxycarbonyldimethylmethyloxy phenyl]prop-2-en-1-one, 1-[4-trifluoromethyloxyphenyl]-3-[3,5-dimethyl-4-carboxydimethylmethyl oxyphenyl]prop-2-en-1-one, 2[2,6-dimethyl-4-[3-[4-(methylthio)phenyl]-3-oxo-propyl] phenoxy]-2-methylpropanoic acid, and 2[2,6-dimethyl-4-[3-[4-(methylthio) phenyl]-3-oxo-propyl]phenoxy]-2-methylpropanoic acid isopropyl ester; or a pharmaceutically acceptable salt thereof. In a further particular embodiment of the invention, the compound of formula (I) is 1-[4-methylthiophenyl]-3-[3,5-dimethyl-4-carboxydimethylmethyloxy phenyl]prop-2-en-1-one or a pharmaceutically acceptable salt thereof.

In particular, the invention relates to a combination product comprising at least an anti-NAFLD, and/or an anti-NASH, and/or an anti-Fibrotic agent for use in a method for treating NAFLD, NASH, active NASH, and/or Liver fibrosis in a subject in need thereof, wherein the subject has been classified as a receiver of said treatment thanks to a method according to the invention.

In a more particular embodiment, the invention relates to the treatment of NAFLD, NASH, Active NASH, and/or Liver fibrosis with a combination product comprising at least one agent selected from the group of anti-NAFLD, anti-NASH and/or anti-fibrotic compounds, or pharmaceutically acceptable salts thereof.

In a more particular embodiment, the invention relates to the treatment of NAFLD, NASH, Active NASH, and/or Liver fibrosis with Elafibranor.

In a further embodiment of the treatment of NASH or liver fibrosis comprises administering NTZ, TZ, vitamin E or pioglitazone, obeticholic acid, elafibranor, selonsertib, saroglitazar and/or cenicrivoc.

In a further embodiment, the treatment of NASH or liver fibrosis comprises administering NTZ or TZ, in particular NTZ.

In a further particular embodiment, a combination treatment is conducted. In another particular embodiment, the treatment of NAFLD, NAFL, NASH, Active NASH, or Liver fibrosis comprises administering Elafibranor combined with one or more other anti-NAFLD, anti-NAFL, anti-NASH or anti-liver fibrosis compound. In yet another embodiment, the treatment of NAFLD, NAFL, NASH, Active NASH, or Liver fibrosis comprises administering Elafibranor combined with at least one compound selected in the group consisting of NTZ, TZ, vitamin E or pioglitazone, obeticholic acid, elafibranor, selonsertib, saroglitazar and cenicrivoc. In yet another embodiment, the treatment of NAFLD, NAFL, NASH, Active NASH, or Liver fibrosis comprises administering Elafibranor combined with NTZ.

Considering the role of micro-RNA in the modulation of gene expression, the results obtained by the inventors also support pathophysiological roles of miR-452 in the development and evolution of NAFLD, NASH and/or liver fibrosis.

Considering the role of micro-RNA in the modulation of gene expression, the results obtained by the inventors also support pathophysiological roles of miR-452 in the development and evolution of NAFL.

The methods of the invention thus can be used to identify specific subpopulations of subjects with NAFLD, NASH and/or liver fibrosis based on circulating levels of miR-452. These subpopulations might have a miR-452 dependent disease which would make these patients responsive to specific drugs acting directly (miR-452 mimetics or mimics, deregulator of miRNA like circular RNA (CircRNA) or anti-miR-452) or indirectly on miR-452 dependent pathways.

The methods of the invention thus can be used to identify specific subpopulations of subjects with NAFL based on circulating levels of miR-452. These subpopulations might have a miR-452 dependent disease which would make these patients responsive to specific drugs acting directly (miR-452 mimetics, deregulator of miRNA like circular RNA (CircRNA) or anti-miR-452) or indirectly on miR-452 dependent pathways.

In addition, from this observation, in a further aspect the invention relates to a miR-452 inhibitor compound for use in the treatment of NAFLD, NASH or liver fibrosis in a subject in need thereof.

In addition, from this observation, in a further aspect the invention relates to a miR-452 inhibitor compound for use in the treatment of NAFL in a subject in need thereof.

As used herein, the term "miR-452 inhibitor compound" and declinations thereof refers to any compound, such as a nucleic acid compound, able to prevent the action of miR-452 and particularly of hsa-miR-452-5p and hsa-miR-452-3p. In a particular embodiment, the miR-452 inhibitor compound of the present invention is a compound that inhibits or reduces the activity of miR-452, for example by binding to miR-452 or that inhibits miR-452 expression. The term "inhibiting miR-452 expression" means that the production of miR-452 in the liver or hepatocytes after treatment with said inhibiting compound is less than the amount produced prior to treatment. One skilled in the art can readily determine whether miR-452 expression has been inhibited in liver or hepatocytes, using for example techniques for determining miRNA transcript level.

Suitable miR-452 inhibitor compounds include double or single-stranded RNA (such as short- or small-interfering RNA or "siRNA"), antagomirs, antisense nucleic acids, circular RNA, artificial miRNA sponges and enzymatic RNA molecules such as ribozymes. Each of these compounds can be targeted to a given miRNA and destroy or induce the destruction of the target miRNA. For example, expression of a given miRNA can be inhibited by inducing RNA interference of the miRNA with an isolated double-stranded RNA ("dsRNA") molecule which has at least 90%, for example 95%, 98%, 99% or 100%, sequence homology with at least a portion, or preferably with the entirety, of the miRNA. In a preferred embodiment, the dsRNA molecule is a siRNA. siRNAs useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target miRNA.

Kits

According to a further aspect, the present invention also relates to a kit comprising means for determining the level of:

(i) miR-452 in a body fluid sample, and, optionally
(ii) at least one other circulating marker of liver damage.

According to another aspect, the present invention also relates to a kit comprising means for determining the level of:

(i) miR-452 in a body fluid sample, and, optionally
(ii) at least one other marker of NAFLD, NASH, or liver Fibrosis.

The kit of the invention is useful for implementing the methods described above. It may further optionally include instructions for implementing said methods. The kit may comprise reagents and buffers appropriate for conducting measures of the levels of miR-452 and any other circulating marker of liver damage as provided above. In particular, the kit may comprise antibodies specific for a protein to be quantified, and/or primers useful for quantifying micro-RNA levels, as well-known in the art.

The kit may comprise reagents and buffers appropriate for conducting measures of the levels of miR-452 and any other marker of NAFLD and/or NASH.

In a preferred embodiment, the kit comprises means for determining the level of miR-452-5p.

It is to be understood that the description above as well as the examples that follow are intended to illustrate and not limit the scope of the invention. Other aspects, advantages and modifications within the scope of the inventions will be apparent to those skilled in the art to which the invention pertains.

EXAMPLES

Materials and Methods
A. Clinical Samples
Blood samples used in this biomarker study were drawn from patients of the GOLDEN-DIAG, OBESE cohort and RESOLVE-It study.

The phase 2 clinical trial GOLDEN-505 (NCT01694849) was a multicentre, randomized, double blind, placebo-controlled study to evaluate the efficacy and safety of Elafibranor (1-[4-methylthiophenyl]-3-[3,5-dimethyl-4-carboxydimethylmethyloxy phenyl]prop-2-en-1-one) once daily on steatohepatitis in patients with Non-Alcoholic Steatohepatitis (NASH). Liver biopsy was performed to confirm the diagnosis of NASH after appropriate exclusion of liver disease of other etiology. NASH was diagnosed as steatohepatitis evaluated by liver biopsy within 6 months before randomization. Steatohepatitis confirmation was based on central reading of liver biopsies. NASH patients were defined with a NAS≥3 including steatosis score≥1 and hepatocyte ballooning≥1 and lobular inflammation≥1. The study was approved by appropriate regulatory bodies all patients had given informed consent for participation.

An inclusion liver biopsy was used for examination and scoring of histological lesions. Blood samples were withdrawn at screening and at the end of the 1-year treatment period for hematology, and clinical biochemistry analysis including a comprehensive list of NAFLD/NASH related parameters. In patients who have signed a dedicated informed consent, additional blood samples were collected for research of new diagnostic biomarkers of NASH.

Blood samples used in this biomarker study were drawn from patients of the GOLDEN-DIAG study at inclusion (270 samples) and one year later (223 samples).

The inventors had also access to human blood samples from subjects with a liver biopsy and associated clinical and biological data from the UZA Biobank, the OBESE cohort. This cohort, which is composed of morbidly obese patients, also comprises NAFLD/non-NASH patients, NASH patients, cirrhotic patients and healthy controls. The serum of 253 patients was processed for the validation of candidate circulating miRNA identified in GOLDEN-DIAG study with next generation sequencing (NGS) technology (HTG EdheSeq) and RT-qPCR respectively. Written, informed consent for collection, storage and use of additional samples was obtained from every patient.

The inventors had also access to human blood samples from subjects with a liver biopsy and associated clinical and biological data from the RESOLVE-IT study. RESOLVE-IT is a Multicenter, Randomized, Double-Blind, Placebo-Controlled Phase III Study (NCT02704403) to Evaluate the Efficacy and Safety of Elafibranor in Patients with Nonalcoholic Steatohepatitis (NASH) and fibrosis. The study was approved by appropriate regulatory bodies all patients had given informed consent for participation. An inclusion liver biopsy was used for examination and scoring of histological lesions. Blood samples were withdrawn at screening. In patients who have signed a dedicated informed consent, additional blood samples were collected for research of new diagnostic biomarkers of NASH.

The serum of 370 patients of the RESOLVE-IT study at screening with 263 corresponding liver biopsy was processed for the validation of candidate circulating miRNA identified in GOLDEN-DIAG study with HTG Edge sequence analysis and RTqPCR analysis.

The serum of 100 subjects from EFS (Etablissement Francais du Sang) was processed for the assessment in healthy subjects of candidate circulating miRNA identified in GOLDEN-DIAG study with HTG Edge sequence analysis. Serum samples were used for the HTG Edge sequence analysis.

The serum samples of the three cohorts (GOLDEN-DIAG, OBESE and RESOLVE-IT) were used for the HTG Edge sequence analysis and RTqPCR analysis.

B. Blood Sampling and Laboratory testing

Blood samples were collected according to the Central Laboratory Protocol and Manual—Genfit—GFT505-212-7.

According to the study protocol, following analyses were performed.

HEMATOLOGY includes hemoglobin, hematocrit, RBC count, leukocytes, differential leukocyte count (neutrophils, lymphocytes, eosinophils, monocytes, basophils-abs. and % values), platelet count and reticulocytes.

BIOCHEMISTRY Panel I includes plasma glucose, triglycerides (TG), creatinine, creatinine clearance, gamma-glutamyltransferase (GGT), aspartate aminotransferase (AST), alanine aminotransferase (ALT), creatine phosphokinase (CPK), alkaline phosphatase, thyroïd stimulating hormone (TSH) and HbA1c.

BIOCHEMISTRY Panel II includes plasma glucose, creatinine, creatinine clearance, total protein, albumin, sodium, potassium, chloride, calcium, uric acid, urea expressed as blood urea nitrogen (BUN), aspartate aminotransferase (AST), alanine aminotransferase (ALT), gamma-glutamyltransferase (GGT), alkaline phosphatase, creatine phosphokinase (CPK), bilirubin total, bilirubin conjugated, C-reactive protein (hsCRP), AST/ALT Ratio and HbA1c.

URINALYSIS includes:
Dipstick analysis (specific gravity, pH, RBC, leukocytes, glucose, protein, ketones, bilirubin, urobilinogen and nitrite)
Microscopy analysis includes RBC, WBC, casts, crystals, bacteria, epithelial cells and yeasts.
Chemistry analysis (albumin and creatinine)

SEROLOGY includes HIV ab I/II, HCV ab, HCV RNA (only tested upon receipt of HCV RNA Visit samples and in case of 'reactive' or 'indeterminate' result for HCV Ab) and HbsAg.

LIPID PANEL includes triglycerides (TG), total cholesterol, non HDL-C (calculation), highdensity lipoprotein cholesterol (HDL-C), low density lipoprotein (LDL-C) (calculation), calculated very low density lipoprotein cholesterol (VLDL-C) (calculation), apolipoprotein AI (ApoAI) and apolipoprotein B (ApoB).

URINE CHEMISTRY includes alpha-1-microglobulin, beta-N-acetylglucosaminidase(beta-NAG) and neutrophil-gelatinase associated lipocalin(N-Gal)

SAFETY MARKERS includes homocysteine, NT-ProBNP, Troponin T, Cystatin C, and Beta2-microglobulin.

GLYCEMIC AND OTHER LIPIDIC PARAMETERS includes leptin, insulin, homeostatic model assessment (HOMA-IR), serum glucose (for calculation of HOMA-IR), fructosamine, Cpeptide and free fatty acids (FFA).

INFLAMMATORY MARKERS includes haptoglobin, fibrinogen, tumor necrosis factor alpha (TNF-α), interleukine 6 (IL-6) and plasminogen activator inhibitor 1 (PAI-1) Ag (citrate).

LIVER MARKERS includes cytokeratin-18 (CK18) (M65 & M30), adinopectin, ferritin, alpha2 macroglobulin, FGF19 & FGF21, hyaluronic acid (Advia centaur, reagentiaprocured by Siemens Belgium and charged to Genfit in pass-through), N-terminal pro-peptide of collagen type III (PIIINP) (Advia centaur, reagentia procured by Siemens Belgium) and tissue inhibitor of matrix metalloprotease-1 (TIMP-1) (Advia centaur, reagentiaprocured by Siemens).

The list of methods, instrument and manufacturer for each biochemical assay is reported in this table:

| Parameter | Method | Instrument | Manufacturer |
|---|---|---|---|
| leptin | ELISA | manually | R&D systems |
| insulin | CLIA | Immulite 2000 | Siemens |
| HOMA-IR | Calculation with Glucose and Insulin | | |
| fructosamine | Colorimetric | Modular P800 | Roche Diagnostics |
| c-Peptide | CLIA | Immulite 2000 | Siemens |
| haptoglobin | immunoturbidimetry | Modular P800 | Roche Diagnostics |
| fibrinogen | Clauss method | STAR-evolution | Stago |
| TNF alpha | fluorokine multi analyte profiling | Luminex | Millipore |
| IL-6 | fluorokine multi analyte profiling | Luminex | Millipore |
| PAI-1 Ag | ELISA | manually | Stago |
| FFA | ACS-ACOD | Modular P800 | Roche Diagnostics |
| CK18 M30 | ELISA | manually | Peviva |
| CK18 M65 | ELISA | manually | Peviva |
| adiponectin | ELISA | manually | Millipore |
| ferritin | ECLIA | Modular E170 | Roche Diagnostics |
| alpha2 macroglobulin | nephelometry | BN II | Siemens |
| hyaluronic acid | immunoassay | Advia centaur | Siemens |
| PIIINP | immunoassay | Advia centaur | Siemens |
| TIMP-1 | immunoassay | Advia centaur | Siemens |
| FGF-19 | ELISA | manually | R&D systems |
| FGF-21 | ELISA | manually | R&D systems |
| visfatin | ELISA | manually | Alpco immunoassays |
| resistin | ELISA | manually | R&D systems |
| YKL-40, CHI3L1 | Human Chitinase 3-like 1 Immunoassay Quantikine ® ELISA Catalog Number DC3L10 For the quantitative determination of human Chitinase 3-like 1 (CHI3L1) concentrations in cell culture supernates, serum, plasma, and urine. | | |

Sample Collection & Storage

Blood samples used in this biomarker study were drawn from patients of the 505.212.7 study before treatment period. Written, informed consent for collection, storage and use of additional samples was obtained from every patient.

Blood collected in citrate containing tubes 2.7 mL was processed by separating cell-free plasma from blood cells within 15 minutes of collection by centrifugation at 1,500×g for 15 minutes. The supernatant plasma was transferred to a new tube. Tubes were kept at −70° C. To proceed to RNA extraction, plasma tubes were then centrifuged at 13,000×g for 2 min to pellet and remove the platelets. The supernatant platelet-free plasma was transferred to a new tube, frozen in liquid nitrogen and stored at −80° C.

Blood collected in serum separating tube (SST) 8.5 mL was processed one hour after 15 sampling by separating cell-free serum from blood cells by centrifugation between 1,300×g and 2,000×g for 10 minutes. The serum was then transferred to a new tube. Tubes were kept at −70° C. RNA extraction was performed without additional centrifugation.

C. Next Generation Sequencing

HTG Edge Sequencing System was used for sequencing the miRNAs contained in serum samples.

Serum levels of 2083 miRNAs (miRBase) were measured using HTG-EdgeSeq-NGS technology. HTG whole transcriptome miRNA (WTA) kit was used.

Samples were prepared using 15 μl of plasma lysis buffer and 15 μl of plasma sample and 3 μl of Proteinase K are mixed and incubated at 50° C. for 60 min with orbital shaking. 25 μl of the mix is transferred to the HTG sample plate and loaded into the HTG processor to perform the nuclease protection assay and prepare the stoichiometric NPP.

Library Preparation and Sequencing

Barcoding is performed using Hemo KlenTaq enzyme. For each sample, we mix 2.4 μl of Hemo KlenTaq, 0.6 μl of dNTPs (10 nM), 6 μl of OneTaq PCR GC Buffer 5×, 3 μl of Forward and Reverse Primers, 3 μl of sample preparation and 12 μl of H20. In order to remove excess of primer from the library, Agentcour AMPure XP beads were used. Library concentration of for each sample was performed using Kapa Biosystems qPCR Kit. Each sample is pooled in order to generate a pooled library and sequenced on an Illumina NextSeq500. For each sample, at least 250.000 reads are generated. Data reconstruction and analysis were performed using FASTQ files and processed by the HTG Parser software.

The levels of miRNAs (number of reads) in serum samples of NASH patients at risk of fibrosis progression (To-Be-Treated; TBT=NAS≥4, F≥2 at histological exam, n=109) were compared to levels obtained in serum of Not-To-Be-Treated (NTBT) patients, n=161. Fold change (TBT vs NTBT) and statistical significance were calculated.

Bioinformatics Analysis

The objective of the analyses is to discover biomarkers that can be related to the identification of NASH patients to be treated. Patients to be treated (TBT) are defined differently according to the different parts of the study.

TBT2 are defined as:
steatosis score≥1
hepatocyte ballooning score≥1
lobular inflammation score≥1
NAS (NAFLD Activity Score)≥4 (NAS is defined as the sum of the steatosis score, hepatocyte ballooning score and lobular inflammation grade)
fibrosis stage≥2 (such as a fibrosis equal to 2, 3 or 4, in particular 2 or 3).

Quality control checks (FastQC) aim to provide a simple way to do some quality control checks on raw sequence data coming from high throughput sequencing pipelines.

It provides a modular set of analyses which you can use to give a quick impression of whether your data has any problems of which you should be aware before doing any further analysis.

HTG whole transcriptome miRNA (WTA) kit was used. Library preparation and sequencing was performed according to manufacturer's recommendations. For each sample, a mean of 931.000 reads per sample were generated. Data were normalized upon the manufacturer's recommendation to allow direct comparison between the different samples by the adjustments of number of reads. Limma, an R/Bioconductor software package, powered differential analyses for HTG Edge Sequencing analyses.

D. Quantitative RTqPCR of miRNA in Serum

Serum Total RNA with preserved miRNAs was extracted from 100 µl of serum by miRVanaParis extraction kit (AM1556, Ambion) according to the manufacturer's instructions. Synthetic spiked-in C. elegans miR-39-3p was added to the samples [3,125 fmoles] (cel-miR-39-3p, miRBase accession number MIMAT=0000010, 5'Phos-UCACCGG-GUGUAAAUCAGCUUG-3' (SEQ ID NO:4), HPLC purified, Integrated DNA Technologies) prior to RNA extraction as internal control of RNA extraction process. The elution was performed in 100 µl of elution buffer.

Expression of mature miRNAs was detected according to the manufacturer's instructions using the Taqman miRNA qRT-PCR Assay: TaqMan MicroRNA Reverse transcription Kit (Ref: 4366597, Applied Biosystems, Carlsbad, CA), TaqMan MicroRNA Assay 20× (Ref: 4440888, Applied Biosystems) and TaqMan Universal Master Mix II (Ref: 4440040, Applied Biosystems).

Reverse transcriptions were performed using a GeneAmp® PCR System 9700 thermal cycler (Ref: 200005, Applied Biosystems).

Quantitative PCRs were performed using a CFX96 Touch™ Real-Time PCR Detection System—C1000—IVD certified, (185-5095 IVD, BioRad).

The sequence of miRNA of interest and Taq Man assay ID is reported in the following table:

| miRNA ID | Sequence | miRbase Number | Assay ID |
| --- | --- | --- | --- |
| hsa-miR-452-5p | AACUGUUUGCAGAGGAAACUGA (SEQ ID NO: 1) | MIMAT0001635 | 001032 |

Synthetic hsa-miRNA (Integrated DNA Technologies) was diluted at 3.125 fmol/mL and 5 µL was used for reverse transcription concurrently with RNA extracted from serum samples. The product was serially diluted and PCR was performed on all samples (standards and serum-derived RNA). Standard curve was performed and used to convert Cq data in copies/µL. The Cq Determination mode was Regression. Quantitation is expressed in copies/µL of serum format.

The supplier is IDT for the synthetic hsa-miRNA.

Results

First, circulating levels of 2083 miRNA species were simultaneously measured in 1216 serum samples from GOLDEN-DIAG, (270 at Inclusion, 223 One Year Later), OBESE (253 samples at inclusion), RESOLVE-IT (370 samples from screening visit) and HEALTHY (100 EFS subjects) through HTG Edge Sequencing for an unbiased selection of miRNAs which circulating levels could discriminate TBT2 patients (TBT2 definition=NAS≥4 and F≥2, and at least one point in steatosis, lobular inflammation and hepatocyte ballooning scores) and NTBT2 subjects (NTBT2 subject differs from a TBT2 subject in at least one point lesser grade in steatosis, hepatocyte ballooning, lobular inflammation scores, NAS and/or fibrosis stage). TBT2 patients should be treated for their increased risk of evolution to serious liver outcomes like cirrhosis, HCC, liver failure, liver transplant and liver death.

From this analysis, the inventors have identified mir-452 which was commonly overexpressed in serum samples of TBT2 patients in comparison to NTBT2 patients in GOLDEN-DIAG, OBESE and RESOLVE-IT cohorts at inclusion.

As shown in the table 1, notably and surprisingly, in GOLDEN-DIAG, OBESE and RESOLVE cohorts, the number of reads per million for hsa-miR-452-5p was significantly higher in TBT2 patients than in NTBT2 patients.

For example, 36 RPM (Reads per million) were obtained in TBT2 patients versus 21 RPM for NTBT2 patients for hsa-miR-452-5p in GOLDEN-DIAG at inclusion.

The inventors also used liver biopsies and serum samples collected at the end of the one-year treatment period of GOLDEN trial as a third independent data set and once again confirmed that the number of reads per million for hsa-miR-452-5p was significantly higher in TBT2 patients than in NTBT2 patients.

These results were confirmed in the independent cohorts OBESE and RESOLVE-IT between TBT2 and NTBT2 patients.

In GOLDEN-DIAG, OBESE and RESOLVE-IT cohorts, hsa-miR-452-5p serum concentrations were significantly higher in NTBT2 (NAFLD patients with minimal histological lesions) than in serum from HEALTHY subjects (Table 1).

TABLE 1

HGT-Edge- Sequencing experiments and number of reads per millions (RPM) obtained for hsa-miR-452-5p in To-Be-Treated (TBT2) versus Not-To-Be-Treated (NTBT2) patients. Reads per million (RPM) are expressed as mean of NTBT2 and TBT2 patient groups (GOLDEN-DIAG Study - At inclusion (109 TBT2 and 161 NTBT2 patients) and Golden Diag - One Year Later (76 TBT2 and 147 NTBT2); OBESE (50 TBT2 and 202 NTBT2 patients); RESOLVE-IT (87 TBT2 and 90 NTBT2) respectively; TBT2 refers to patients with NAS ≥ 4 with at least 1 point in Steatosis, Hepatocyte Ballooning and Lobular Inflammation scores and fibrosis stage ≥ 2 at histological examination of a liver biopsy. NTBT2 subject differs from a TBT2 subject in at least one point lesser grade in steatosis, hepatocyte ballooning, lobular inflammation scores, NAS and/or fibrosis stage. HEALTHY subjects are 100 EFS subjects without medication, RPM are expressed as mean of the 100 subjects. EFS (Etablissement Français du Sang) subjects are healthy subjects without medication.

| hsa_miRNA | RPM in NTBT2 | RPM in TBT2 | Fold Change | p value |
|---|---|---|---|---|
| GOLDEN-DIAG - At inclusion | | | | |
| hsa-miR-452-5p | 21 | 36 | 1.61 | 1.24E−05 |
| GOLDEN-DIAG- One Year Later | | | | |
| hsa-miR-452-5p | 21 | 40 | 1.97 | 1.83E−08 |
| OBESE | | | | |
| hsa-miR-452-5p | 10 | 17 | 1.60 | 5.50E−04 |
| RESOLVE-IT At inclusion | | | | |
| hsa-miR-452-5p | 23 | 32 | 1.53 | 1.14E−04 |
| HEALTHY | | | | |
| hsa_miRNA | RPM | | | |
| hsa-miR-452-5p | 6 | | | |

For confirmation, levels of hsa-mir-452-5p were then measured using the gold standard method for quantitation of oligonucleotides in body fluids, RT-qPCR, using specific Taq Man miRNA assays. Result can be resumed as follows:

As shown in table 2 and FIGS. 1-2-3-4, in the three cohorts at inclusion and in GOLDEN-DIAG at week-52, hsa-mir-452-5p serum concentration was significantly higher in TBT2 patients than in NTBT2 patients.

TABLE 2

RT-qPCR experiments for confirmation/validation of overexpression of hsa-miR-452-5p in To Be Treated (TBT2) Patients versus Not-To-Be-Treated (NTBT2) Patients. Statistical significance TBT2 vs NTBT2 was calculated using the non-parametric Mann Whitney test. TBT2 refers to patients with NAS ≥4 with steatosis, hepatocyte ballooning and lobular inflammation scores ≥1 and fibrosis stage ≥2 at histological examination of a liver biopsy. AUC = Area under the curve of Receiver Operating Characteristic were obtained for identification of TBT2 vs NTBT2.

| RT-quantitative PCR | Copies.µL-1 in NTBT2 | | | Copies.µL-1 in TBT2 | | | TBT2/NTBT2 | | |
|---|---|---|---|---|---|---|---|---|---|
| Copies.µL-1 Serum | Mean levels | SD | SEM | Mean levels | SD | SEM | Fold Change | p value | AUC |
| GOLDEN-DIAG - At Inclusion | | | | | | | | | |
| hsa-miR-452-5p | 12 | 11 | 1 | 23 | 17 | 2 | 1.84 | <0.0001 | 0.72 |
| GOLDEN-DIAG - One Year Later | | | | | | | | | |
| hsa-miR-452-5p | 13 | 10 | 1 | 23 | 18 | 2 | 1.77 | <0.0001 | 0.71 |
| OBESE | | | | | | | | | |
| hsa-miR-452-5p | 13 | 8 | 1 | 24 | 19 | 3 | 1.83 | <0.0001 | 0.72 |
| RESOLVE-IT | | | | | | | | | |
| hsa-miR-452-5p | 14 | 12 | 1 | 27 | 25 | 2 | 1.93 | <0.0001 | 0.73 |

Figure 1:
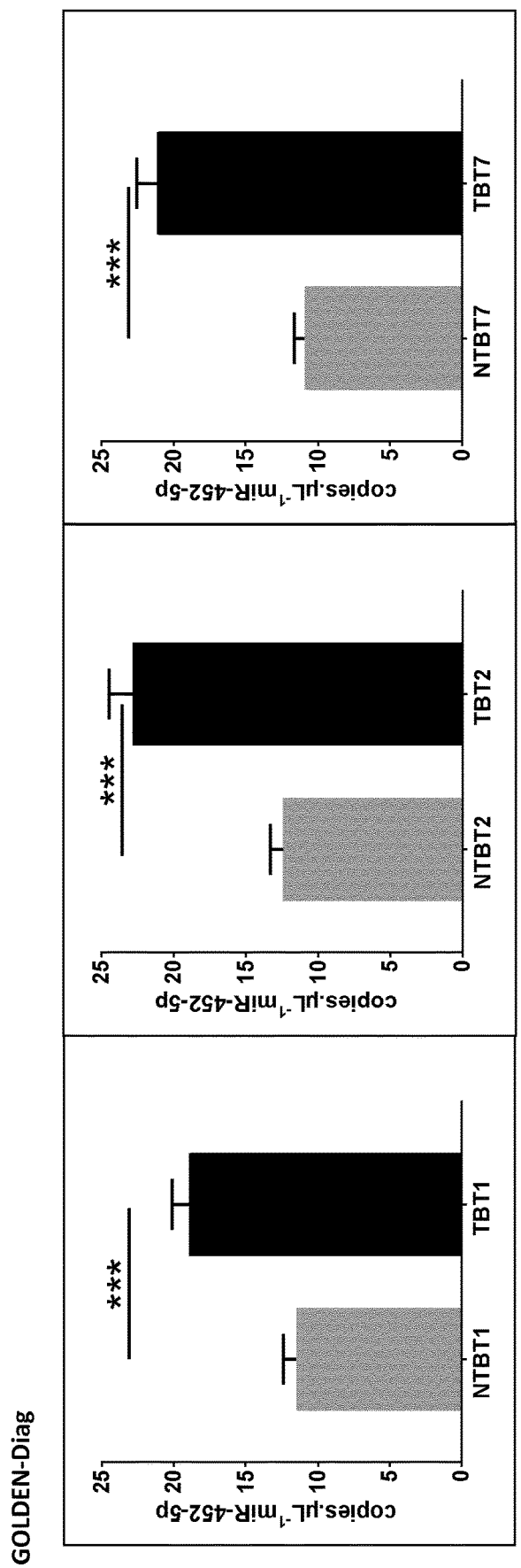
FIG. 1: Serum level of hsa-miR-452-5p in Not-To-Be Treated (NTBT) and To-Be-Treated (TBT) patients of GOLDEN-DIAG according to three different definitions of TBT patients: TBT1, TBT2 and TBT7. NTBT1 n=83, TBT1 n=187; NTBT2 n=169, TBT2 n=101, NTBT7 n=119, TBT7 n=151. Results are expressed as Mean±SEM. Statistical significance was calculated using Mann Whitney test: ***, p value<0.001.

As shown in FIG. 1 when applying a second definition of TBT patients and NTBT patients (TBT1 vs. NTNT1) in the GOLDEN-DIAG cohort at inclusion, analyses showed that hsa-miR-452-5p serum concentration was significantly higher in TBT1 patients than in NTBT1 patients. In these analyses, TBT1 refers to patients with NAS≥4 with at least 1 point in steatosis, hepatocyte Ballooning and Lobular Inflammation scores and fibrosis stage≥1 at histological examination of a liver biopsy. A NTBT1 subject differs from a TBT1 subject in at least one point lesser grade in steatosis, hepatocyte ballooning, lobular inflammation scores, NAS and/or fibrosis stage.

As shown in FIG. 1 when applying a third definition of TBT patients and NTBT patients (TBT7 vs. NTBT7) in the GOLDEN-DIAG cohort at inclusion, analyses showed that hsa-miR-452-5p serum concentration was significantly higher in TBT7 patients than in NTBT7 patients. In these analyses, TBT7 refers to patients with NAS≥4 with at least 1 point in steatosis, hepatocyte ballooning and Lobular Inflammation scores and fibrosis stage≥1 at histological examination of a liver biopsy. A NTBT1 subject differs from a TBT1 subject in at least one point lesser grade in steatosis, hepatocyte ballooning, lobular inflammation scores, NAS and/or fibrosis stage.

As shown in FIGS. 2, 3 and 4, in the three cohorts, hsa-miR-452-5p serum concentrations were significantly higher in patients with Active-NASH (NAS≥4 with at least one point in steatosis, lobular inflammation and hepatocyte ballooning) than in non-NASH and mild NASH patients (NAS<4).

As shown in FIGS. 2, 3 and 4, in the three cohorts, hsa-mir-452-5p serum concentrations were significantly higher in patients with significant fibrosis or higher fibrosis stage (F≥2) than in patients with no or minimal fibrosis (F<2). Further analyses of RT-qPCR experiments performed on serum samples from GOLDEN-DIAG at inclusion showing strong correlations between circulating levels of miR-452 species and histological scores and fibrosis stage are provided (similar results were obtained using OBESE and RESOLVE-IT samples):

As shown in FIG. 5, circulating level of hsa-miR-452-5p positively correlated with steatosis score, lobular inflammation score, hepatocyte ballooning score. Consequently, circulating level of miR-452-5p significantly and positively correlated with NAS and activity Index. Finally, there was a strong correlation between circulating level of miR-452-5p and fibrosis stage.

The results presented in the following table 3 illustrate significant correlations between changes in circulating levels of hsa-miR-452-5p and evolution of NAS, NASH Activity Index and Fibrosis after 52 weeks in GOLDEN patients.

TABLE 3

Correlation of changes in serum levels of hsa-miR-452-5p and the evolutions of Activity Index (AI), NAS and Fibrosis during the one-year GOLDEN trial.

GOLDEN-DIAG (Week52-Inclusion)
Change in miR serum concentration (ΔmiR) vs Evolution of Activity Index (ΔAI)

|  | Improvement (ΔAKO) | Stable (ΔAI = 0) | Worsening (ΔAI > 0) | P Value (Kruskal Wallis test) |
|---|---|---|---|---|
| ΔmiR-452-5p (copies · µL$^{-1}$) | −1.81 ± 1.54 | 1.237 ± 1.61 | 0.56 ± 2.26 | 0.2124 |

GOLDEN-DIAG (Week52-Inclusion)
Change in miR serum concentration (ΔmiR) vs Evolution of NAS (ΔNAS)

|  | Improvement (ΔNAS < 0) | Stable (ΔNAS = 0) | Worsening (ΔNAS > 0) | P Value (Kruskal Wallis test) |
|---|---|---|---|---|
| ΔmiR-452-5p (copies · µL$^{-1}$) | −2.39 ± 1.60 | 2.069 ± 1.64 | 0.8237 ± 1.95 | 0.055 |

GOLDEN-DIAG (Week52-Inclusion)
Change in miR serum concentration (ΔmiR) vs Evolution of Fibrosis (ΔF)

|  | Improvement (ΔF < 0) | Stable (ΔF = 0) | Worsening (ΔF > 0) | P Value (Kruskal Wallis test) |
|---|---|---|---|---|
| ΔmiR-452-5p (copies · µL$^{-1}$) | −1.491 ± 1.45 | −0.23 ± 1.32 | 1.01 ± 3.15 | 0.7550 |

In conclusion:
i) these results, based on measurement of levels of miRNA in serum and plasma samples using two different methodologies (HTG Edge-Seq and RTqPCR) support the use of hsa-mir-452-5p and more generally hsa-miR-452 related oligonucleotides as circulating diagnostic biomarkers for identification of patients with NAFLD (NAS≥1), NASH (NAS≥3 with at least 1 point in steatosis, at least 1 point in lobular inflammation and at least 1 point in hepatocyte ballooning scores), Active-NASH (NAS≥4 with at least 1 point in steatosis, at least 1 point in lobular inflammation and at least 1 point in hepatocyte ballooning scores), significant fibrosis (F≥2), and/or Active-NASH and fibrosis (TBT1, TBT2, TBT7).
ii) these results, based on measurement of levels of miRNA in serum samples support the use of hsa-miR-452 species as circulating diagnostic biomarkers for non-invasive grading of histological lesions (steatosis, lobular inflammation, hepatocyte ballooning), assessment of NASH activity (NAS or Activity Index) and assessment of disease severity (fibrosis stage) in a subject.
iii) these results, based on measurement of levels of miRNA in serum and plasma samples support the use of hsa-miR-452 species as circulating diagnostic biomarkers for non-invasive grading of histological lesions (steatosis, lobular inflammation, hepatocyte ballooning), assessment of NASH activity (NAS or Activity Index) and assessment of disease severity (fibrosis stage) in a subject.
iv) these results, based on measurement of levels of miRNA in serum and plasma samples support the use of hsa-miR-452 species as circulating biomarkers for monitoring evolution of NAFLD activity, NASH activity or fibrosis stage in a same patient either the patient is treated or not with an anti-NAFLD drug, an anti-NASH drug or an anti-fibrotic drug.
v) Finally, the state of art linking the level of NASH activity to the risk of fibrosis evolution and linking fibrosis stage to risk of long term liver outcomes (cirrhosis, liver transplant, HCC or liver death), support miR-452 species as prognostic biomarkers for evaluating the risk of fibrosis evolution to cirrhosis and for estimating the risk of long term serious complications.

REFERENCES

Castoldi M, Benes V, Hentze M W, Muckenthaler M U (2007) miChip: a microarray platform for expression profiling of microRNAs based on locked nucleic acid (LNA) oligonucleotide capture probes. Methods 43: 146-152

Chen C, Ridzon D A, Broomer A J, Zhou Z, Lee D H, Nguyen J T, Barbisin M, Xu N L, Mahuvakar V R, Andersen M R, Lao K Q, Livak K J, Guegler K J (2005) Real-time quantification of microRNAs by stem-loop RT-PCR. Nucleic Acids Res 33: e179

Dulai P S, Singh S, Patel J, Soni M, Prokop L J, Younossi Z, Sebastiani G, Ekstedt M, Hagstrom H, Nasr P, Stal P, Wong V W, Kechagias S, Hultcrantz R, Loomba R (2017) Increased risk of mortality by fibrosis stage in nonalcoholic fatty liver disease: Systematic review and meta-analysis. Hepatology 65: 1557-1565

Ekstedt M, Hagstrom H, Nasr P, Fredrikson M, Stal P, Kechagias S, Hultcrantz R (2015) Fibrosis stage is the strongest predictor for disease-specific mortality in NAFLD after up to 33 years of follow-up. Hepatology 61: 1547-1554

Geiss G K, Bumgarner R E, Birditt B, Dahl T, Dowidar N, Dunaway D L, Fell H P, Ferree S, George R D, Grogan T, James J J, Maysuria M, Mitton J D, Oliveri P, Osborn J L, Peng T, Ratcliffe A L, Webster P J, Davidson E H, Hood L, Dimitrov K (2008) Direct multiplexed measurement of gene expression with color-coded probe pairs. Nat Biotechnol 26: 317-325

Hafner M, Renwick N, Farazi T A, Mihailovic A, Pena J T, Tuschl T (2012) Barcoded cDNA library preparation for small RNA profiling by next-generation sequencing. Methods 58: 164-170

Lizarraga D, Huen K, Combs M, Escudero-Fung M, Eskenazi B, Holland N (2016) miRNAs differentially expressed by next-generation sequencing in cord blood buffy coat samples of boys and girls. Epigenomics 8: 1619-1635

Miotto E, Saccenti E, Lupini L, Callegari E, Negrini M, Ferracin M (2014) Quantification of circulating miRNAs by droplet digital PCR: comparison of EvaGreen- and TaqMan-based chemistries. Cancer Epidemiol Biomarkers Prev 23: 2638-2642

Nelson P T, Baldwin D A, Kloosterman W P, Kauppinen S, Plasterk R H, Mourelatos Z (2006) RAKE and LNA-ISH reveal microRNA expression and localization in archival human brain. RNA 12: 187-191

Satake E, Pezzolesi M G, Md Dom Z I, Smiles A M, Niewczas M A, Krolewski A S (2018) Circulating miRNA Profiles Associated With Hyperglycemia in Patients With Type 1 Diabetes. Diabetes 67: 1013-1023

Vigneault F, Ter-Ovanesyan D, Alon S, Eminaga S, D C C, Seidman J G, Eisenberg E, G M C (2012) High-throughput multiplex sequencing of miRNA. Curr Protoc Hum Genet Chapter 11: Unit 11 12 11-10

Wong V W, Adams L A, de Ledinghen V, Wong G L, Sookoian S (2018) Noninvasive biomarkers in NAFLD and NASH—current progress and future promise. Nat Rev Gastroenterol Hepatol

---

---

The invention claimed is:

1. A method for diagnosing and treating a non-alcoholic fatty liver disease (NAFLD), non-alcoholic steatohepatitis (NASH) and/or liver fibrosis in a subject, the method comprising:
   (i) measuring the level(s) of miR-452 in one or more body fluid samples of said subject, wherein the one or more body fluid samples is/are one or more of plasma samples or serum samples;
   (ii) diagnosing NAFLD, NASH, and/or liver fibrosis based on the level(s) of miR-452 measured in step (i), wherein an increase of the level of measured miR-452 as compared to a reference level indicates presence of NAFLD, NASH, and/or liver fibrosis in the subject; and (iii) administering to the subject diagnosed in step (ii) an effective amount of a compound, which is selected from the group consisting of:

a compound of formula (I) or a pharmaceutically acceptable salt thereof:

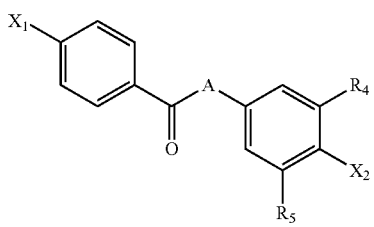

(I)

wherein:
X1 is a halogen atom, a R1 group or G1—R1 group;
A is a CH═CH or CH2—CH2 group;
X2 is a G2—R2 group;
G1 is an atom of oxygen;
G2 is an atom of oxygen or sulfur;
R1 is a hydrogen atom, an unsubstituted alkyl group, an aryl group or an alkyl group that is substituted by one or more substituents selected from halogen atoms, alkoxy groups, alkylthio groups, cycloalkyl groups, cycloalkylthio groups and heterocyclic groups;
R2 is an alkyl group substituted by a —COOR3 group, wherein R3 is a hydrogen atom or an alkyl group that is substituted or not by one or more substituents selected from halogen atoms, cycloalkyl groups and heterocyclic groups; and
R4 and R5, identical or different, are an alkyl group that is substituted or not by one or more substituent selected from halogen atoms, cycloalkyl groups and heterocyclic groups;

AMP activated protein kinase stimulators;
Bile acids;
CCR antagonists;
Dipeptidyl peptidase IV (DPP4) inhibitors;
Farnesoid X receptor (FXR) agonists;
Fibroblast Growth Factor 19 (FGF-19) receptor ligand or functional engineered variant of FGF-19;
Fibroblast Growth Factor 21 (FGF-21) agonists;
engineered Fibroblast Growth Factor 19 (FGF-19) analogues;
Glucagon-like peptide-1 (GLP-1) analogs;
Nicotinic acid;
nitazoxanide (NTZ), its active metabolite tizoxanide (TZ) or other prodrugs of TZ;
PPAR alpha agonists;
PPAR gamma agonists;
PPAR delta agonists;
PPAR alpha/gamma dual agonists (also named glitazars);
PPAR gamma/delta dual agonists;
PPAR alpha/gamma/delta pan agonists or PPARpan agonists;
Sodium-glucose transport (SGLT) 2 inhibitors;
stearoyl CoA desaturase-1 inhibitors/fatty acid bile acid conjugates;
thyroid receptor β (THR β) agonists, and Vitamin E and isoforms, vitamin E combined with vitamin C and atorvastatin.

2. The method according to claim 1, wherein miR-452 is hsa-miR-452.

3. The method according to claim 1, comprising determining the level of hsa-miR-452-5p.

4. The method according to claim 1, wherein the reference level is obtained in samples from healthy subjects with no hepatic steatosis; and wherein if the level of miR-452 of said subject is higher than the reference level, it indicates the presence of NAFLD in said subject.

5. The method according to claim 1, wherein the reference level is obtained in samples from a non-NASH subject; and wherein if the level of miR-452 of said subject is higher than the reference level, it indicates the presence of NASH defined as at least one point in steatosis, lobular inflammation and hepatocyte ballooning score in said subject.

6. The method according to claim 1, wherein the reference level is obtained in samples from subjects without Active-NASH; and wherein if the level of miR-452 of said subject is higher than the reference level, it indicates the presence of Active-NASH defined as NAS≥4 with at least one point in steatosis, one point in lobular inflammation and one point in the hepatocyte ballooning scores in said subject.

7. The method according to claim 1 wherein the reference level is obtained in samples from subjects with no or minimal liver fibrosis (F=0 or 1); and wherein if the level of miR-452 of said subject is higher than the reference level, it indicates the presence of a significant (F=2), moderate (F=3) or severe (F=4) liver fibrosis in said subject.

8. The method according to claim 1, wherein said compound is of formula (I):

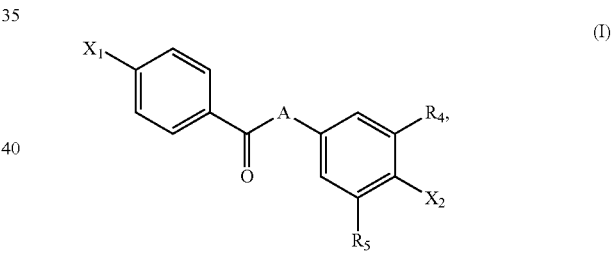

(I)

or a pharmaceutically acceptable salt thereof;
wherein:
X1 is a halogen, a R1, or a G1—R1 group;
A is a CH═CH or a CH2—CH2 group;
X2 is a G2—R2 group;
G1 is an atom of oxygen;
G2 is an atom of oxygen or sulfur;
R1 is a hydrogen atom, an unsubstituted alkyl group, an aryl group or an alkyl group that is substituted by one or more halogen atoms, an alkoxy or an alkylthio group, cycloalkyl groups, cycloalkylthio groups or heterocyclic groups;
R2 is an alkyl group substituted by at least a —COOR3 group, wherein R3 represents a hydrogen atom, or an alkyl group that is substituted or not by one or more halogen atoms, cycloalkyl groups, or heterocyclic groups; and
R4 and R5, identical or different, is an alkyl group that is substituted or not by one or more halogen atoms, cycloalkyl groups, heterocyclic groups.

9. The method according to claim 1, wherein the compound is nitazoxanide.

10. The method according to claim 9, wherein the method further comprises administering to the subject vitamin E or pioglitazone, obeticholic acid, selonsertib, saroglitazar or cenicrivoc.

11. The method of claim 1, further comprising administering to the subject an effective amount of another molecule, which is selected from the group consisting of nitazoxanide, vitamin E or pioglitazone, obeticholic acid, selonsertib, saroglitazar and cenicrivoc.

12. The method of claim according to claim 1, wherein the compound is selected in the group consisting of: PXL-770, MB-11055, Debio-0930B, metformin, CNX-012, O-304, mangiferin calcium salt, eltrombopag, carotuximab, imeglimin, obeticholic acid (OCA), ursodeoxycholic acid (UDCA), norursodeoxycholic acid, ursodiol, cenciriviroc, PG-092, RAP-310, INCB-10820, RAP-103, PF-04634817, CCX-872, evogliptin, vidagliptin, fotagliptin, alogliptin, saxagliptin, tilogliptin, anagliptin, sitagliptin, retagliptin, melogliptin, gosogliptin, trelagliptin, teneligliptin, dutogliptin, linagliptin, gemigliptin, yogliptin, betagliptin, imigliptin, omarigliptin, vidagliptin, denagliptin, tropifexor, cilofexor, nidufexor, EDP-305, AKN-083, INT-767, GNF-5120, LY2562175, INV-33, NTX-023-1, EP-024297, Px-103, SR-45023, TERN-101, TERN-201, TERN-501 and TERN-301; PEG-FGF21, YH-25348, BMS-986171, YH-25723, LY-3025876, NNC-0194-0499, NGM-282, semaglutide, liraglutide, exenatide, albiglutide, dulaglutide, lixisenatide, loxenatide, efpeglenatide, taspoglutide, MKC-253, DLP-205, ORMD-0901, niacin, Vitamin B3, RM-5061, fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, SR10171, pioglitazone, deuterated pioglitazone, rosiglitazone, efatutazone, ATx08-001, OMS-405, CHS-131, THR-0921, SER-150-DN, KDT-501, GED-0507-34-Levo, CLC-3001, ALL-4; GW501516, MBX8025, GW0742, L165041, HPP-593, NCP-1046, saroglitazar, aleglitazar, muraglitazar, tesaglitazar, DSP-8658, conjugated linoleic acid (CLA), T3D-959, IVA337, tetradecylthioacetic acid (TTA), bavachinin, GW4148, GW9135, bezafibrate, lanifibranor, lobeglitazone, CS038, licoglifozin, remogliflozin, dapagliflozin, empagliflozin, ertugliflozin, sotagliflozin, ipragliflozin, tianagliflozin, canagliflozin, tofogliflozin, janagliflozin, bexagliflozin, luseogliflozin, sergliflozin, HEC-44616, AST-1935, PLD-101, aramchol, GRC-9332, steamchol, TSN-2998, GSK-1940029, XEN-801, VK-2809, resmetirom, MGL-3745, SKL-14763, sobetirome, BCT-304, ZYT-1, MB-07811 and eprotirome.

\* \* \* \* \*

SEQUENCE LISTING

```
<160> NUMBER OF SEQ ID NOS: 4

<210> SEQ ID NO 1
<211> LENGTH: 22
<212> TYPE: RNA
<213> ORGANISM: homo sapiens

<400> SEQUENCE: 1
aacuguuugc agaggaaacu ga                                      22

<210> SEQ ID NO 2
<211> LENGTH: 22
<212> TYPE: RNA
<213> ORGANISM: homo sapiens

<400> SEQUENCE: 2
cucaucugca aagaaguaag ug                                      22

<210> SEQ ID NO 3
<211> LENGTH: 85
<212> TYPE: RNA
<213> ORGANISM: homo sapiens

<400> SEQUENCE: 3
gcuaagcacu uacaacuguu ugcagaggaa acugagacuu uguaacuaug ucucagucuc    60
aucugcaaag aaguaagugc uuugc                                          85

<210> SEQ ID NO 4
<211> LENGTH: 22
<212> TYPE: RNA
<213> ORGANISM: Caenorhabditis elegans

<400> SEQUENCE: 4
ucaccgggug uaaaucagcu ug                                      22
```